US012577309B2

(12) United States Patent
Du et al.

(10) Patent No.: US 12,577,309 B2
(45) Date of Patent: Mar. 17, 2026

(54) ANTI-CSF1R MOLECULES AND USE THEREOF

(71) Applicants: Adagene (Suzhou) Limited, Suzhou (CN); Dragonboat Biopharmaceutical (Shanghai) Co., Ltd., Shanghai (CN)

(72) Inventors: Fangyong Du, Suzhou (CN); Peter Peizhi Luo, Suzhou (CN); Yan Li, Suzhou (CN); Guizhong Liu, Suzhou (CN); Xiaohong She, Suzhou (CN); Zhengxi Dai, Suzhou (CN)

(73) Assignee: DRAGONBOAT BIOPHARMACEUTICAL (SHANGHAI) CO., LTD., Shanghai (CN)

( * ) Notice: Subject to any disclaimer, the term of this patent is extended or adjusted under 35 U.S.C. 154(b) by 937 days.

(21) Appl. No.: 17/788,106

(22) PCT Filed: Dec. 23, 2020

(86) PCT No.: PCT/CN2020/138663
§ 371 (c)(1),
(2) Date: Jun. 22, 2022

(87) PCT Pub. No.: WO2021/129673
PCT Pub. Date: Jul. 1, 2021

(65) Prior Publication Data
US 2023/0203170 A1 Jun. 29, 2023

(30) Foreign Application Priority Data
Dec. 24, 2019 (WO) ............... PCT/CN2019/127778

(51) Int. Cl.
*C07K 16/28* (2006.01)
*A61K 39/00* (2006.01)
*A61P 35/00* (2006.01)

(52) U.S. Cl.
CPC .... *C07K 16/2866* (2013.01); *A61K 2039/505* (2013.01); *A61P 35/00* (2018.01); *C07K 2317/24* (2013.01); *C07K 2317/524* (2013.01); *C07K 2317/565* (2013.01); *C07K 2317/73* (2013.01); *C07K 2317/76* (2013.01); *C07K 2317/92* (2013.01); *C07K 2317/94* (2013.01)

(58) Field of Classification Search
CPC ............ C07K 16/2866; C07K 2317/24; C07K 2317/524; C07K 2317/73; C07K 2317/76; C07K 2317/92; C07K 2317/94; C07K 2317/21; C07K 2317/33; A61K 2039/505; A61P 35/00; A61P 35/04
See application file for complete search history.

(56) References Cited

U.S. PATENT DOCUMENTS

| | | | |
|---|---|---|---|
| 5,202,238 A | 4/1993 | Fell, Jr. et al. |
| 5,204,244 A | 4/1993 | Fell |
| 8,206,715 B2 | 6/2012 | Wong et al. |
| 2011/0165156 A1 | 7/2011 | Dimoudis et al. |
| 2011/0274683 A1 | 11/2011 | Wong et al. |

FOREIGN PATENT DOCUMENTS

| | | |
|---|---|---|
| CN | 109096397 A | 12/2018 |
| EP | 0307434 B1 | 9/1993 |
| EP | 2949670 A1 | 12/2015 |
| EP | 3549599 A1 | 10/2019 |
| WO | 98/52976 A1 | 11/1998 |
| WO | 2011/140249 A2 | 11/2011 |
| WO | 2013/132044 A1 | 9/2013 |
| WO | 2016/189045 A1 | 12/2016 |
| WO | 2018/213665 A1 | 8/2018 |
| WO | 2019/036842 A1 | 2/2019 |
| WO | 2019/036856 A1 | 2/2019 |
| WO | 2018/157164 A1 | 8/2019 |

OTHER PUBLICATIONS

Gomez-Roca CA, et al. Phase I study of RG7155, a novel anti-CSF1R antibody, in patients with advanced/metastatic solid tumors . . . J Clin Oncol 33, 3005-3005(2015). DOI:10.1200/jco.2015.33.15_suppl.3005 (Year: 2015).*
Florent Peyraud et al., "CSF-1R Inhibitor Development: Current Clinical Status", Current Oncology Reports, vol. 19, No. 11, Sep. 5, 2017. pp. 1-10.

* cited by examiner

*Primary Examiner* — Maher M Haddad
*Assistant Examiner* — Alec Jon Peters
(74) *Attorney, Agent, or Firm* — Quarles & Brady LLP

(57) ABSTRACT
The disclosure relates to antibodies against human CSF-1R, methods for their production, pharmaceutical compositions containing said antibodies, and uses thereof.

10 Claims, 11 Drawing Sheets
Specification includes a Sequence Listing.

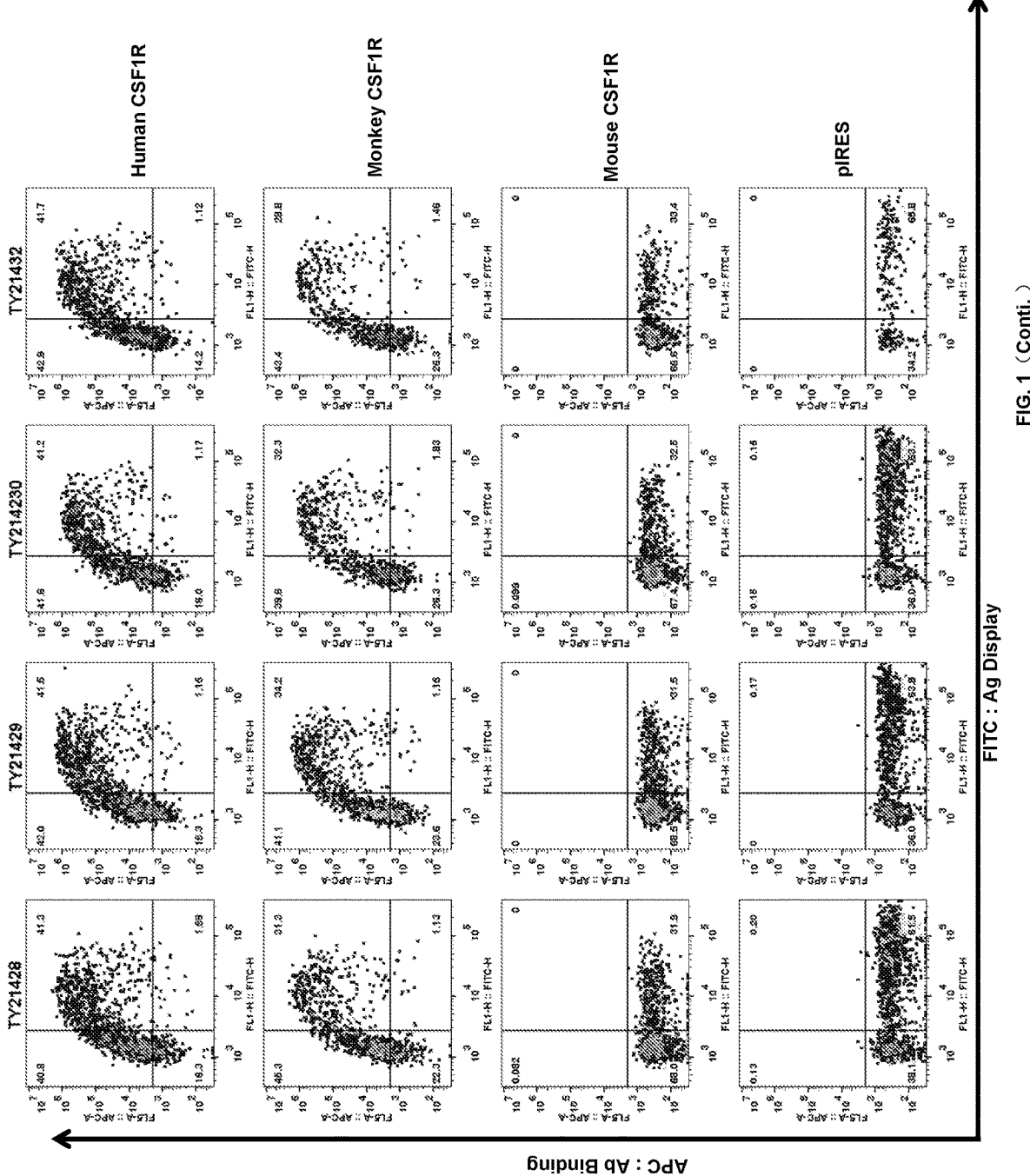
FIG. 1 (Conti.)

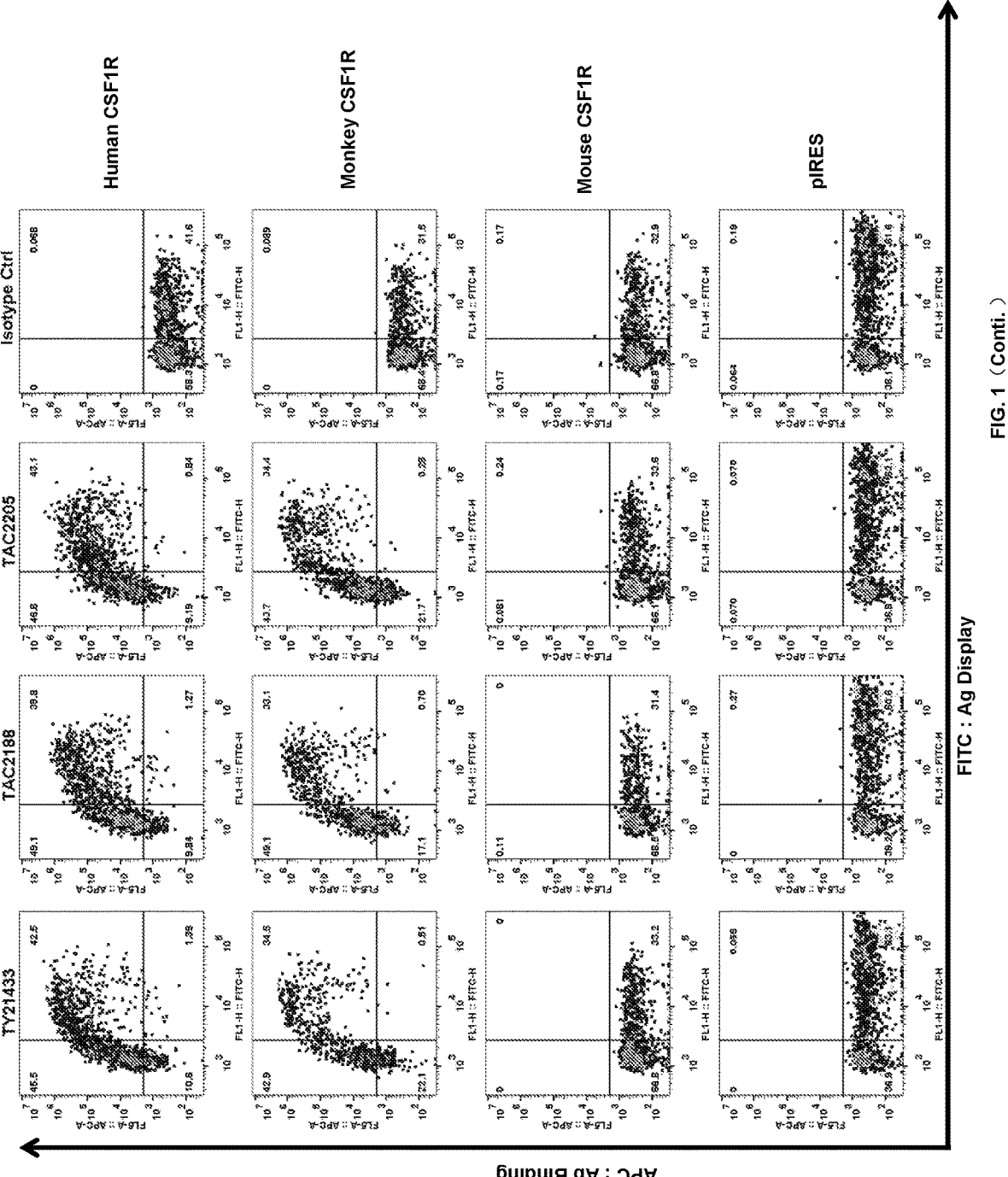
FIG. 1 (Conti.)

SEQUENCE LISTING

```
<160> NUMBER OF SEQ ID NOS: 87

<210> SEQ ID NO 1
<211> LENGTH: 11
<212> TYPE: PRT
<213> ORGANISM: Artificial
<220> FEATURE:
<223> OTHER INFORMATION: Synthetic Construct

<400> SEQUENCE: 1

Phe Thr Phe Ser Gly Tyr Ala Ile His Trp Val
1               5                   10

<210> SEQ ID NO 2
<211> LENGTH: 11
```

```
<212> TYPE: PRT
<213> ORGANISM: Artificial
<220> FEATURE:
<223> OTHER INFORMATION: Synthetic Construct

<400> SEQUENCE: 2

Tyr Thr Phe Ser Asp Tyr Ala Ile His Trp Val
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic Construct

<400> SEQUENCE: 3

Tyr Ser Ile Ser Ser Gly Tyr Tyr Trp Gly Trp Ile
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic Construct

<400> SEQUENCE: 4

Phe Thr Phe Ser Asp Tyr Ala Ile His Trp Val
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic Construct

<400> SEQUENCE: 5

Phe Thr Phe Ser Asn Tyr Gly Ile His Trp Val
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic Construct

<400> SEQUENCE: 6

Tyr Thr Phe Ser Asn Tyr Ala Ile His Trp Val
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic Construct

<400> SEQUENCE: 7

Tyr Ser Ile Thr Ser Gly His His Trp Ala Trp Ile
1               5                   10

<210> SEQ ID NO 8
<211> LENGTH: 11
<212> TYPE: PRT
```

-continued

<213> ORGANISM: Artificial
<220> FEATURE:
<223> OTHER INFORMATION: Synthetic Construct

<400> SEQUENCE: 8

Phe Thr Phe Thr Asp Tyr Ala Ile His Trp Val
1               5                   10

<210> SEQ ID NO 9
<211> LENGTH: 11
<212> TYPE: PRT
<213> ORGANISM: Artificial
<220> FEATURE:
<223> OTHER INFORMATION: Synthetic Construct

<400> SEQUENCE: 9

Tyr Thr Phe Ser Ser Tyr Ala Ile His Trp Val
1               5                   10

<210> SEQ ID NO 10
<211> LENGTH: 11
<212> TYPE: PRT
<213> ORGANISM: Artificial
<220> FEATURE:
<223> OTHER INFORMATION: Synthetic Construct

<400> SEQUENCE: 10

Phe Thr Phe Ser Asn Tyr Ala Ile His Trp Val
1               5                   10

<210> SEQ ID NO 11
<211> LENGTH: 21
<212> TYPE: PRT
<213> ORGANISM: Artificial
<220> FEATURE:
<223> OTHER INFORMATION: Synthetic Construct

<400> SEQUENCE: 11

Val Ser Val Ile Ser Gly Tyr Gly Ser Ser Thr Tyr Tyr Ala Asp Ser
1               5                   10                  15

Val Lys Gly Arg Phe
            20

<210> SEQ ID NO 12
<211> LENGTH: 21
<212> TYPE: PRT
<213> ORGANISM: Artificial
<220> FEATURE:
<223> OTHER INFORMATION: Synthetic Construct

<400> SEQUENCE: 12

Val Ser Val Ile Ser Gly Tyr Gly Ser Thr Thr Tyr Tyr Ala Asp Ser
1               5                   10                  15

Val Lys Gly Arg Phe
            20

<210> SEQ ID NO 13
<211> LENGTH: 21
<212> TYPE: PRT
<213> ORGANISM: Artificial
<220> FEATURE:
<223> OTHER INFORMATION: Synthetic Construct

<400> SEQUENCE: 13

Val Ser Ser Ile Ser Gly Tyr Gly Ser Ser Thr Tyr Tyr Ala Asp Ser
1               5                   10                  15

-continued

```
Val Lys Gly Arg Phe
          20

<210> SEQ ID NO 14
<211> LENGTH: 21
<212> TYPE: PRT
<213> ORGANISM: Artificial
<220> FEATURE:
<223> OTHER INFORMATION: Synthetic Construct

<400> SEQUENCE: 14

Val Ser Val Ile Ser Gly Tyr Gly Gly Ser Thr Tyr Tyr Ala Asp Ser
1               5                   10                  15

Val Lys Gly Arg Phe
          20

<210> SEQ ID NO 15
<211> LENGTH: 21
<212> TYPE: PRT
<213> ORGANISM: Artificial
<220> FEATURE:
<223> OTHER INFORMATION: Synthetic Construct

<400> SEQUENCE: 15

Val Ser Val Ile Ser Gly Tyr Gly Gly Ser Thr Tyr Tyr Ala Asp Ser
1               5                   10                  15

Val Lys Gly Arg Phe
          20

<210> SEQ ID NO 16
<211> LENGTH: 21
<212> TYPE: PRT
<213> ORGANISM: Artificial
<220> FEATURE:
<223> OTHER INFORMATION: Synthetic Construct

<400> SEQUENCE: 16

Val Ser Ala Ile Ser Gly Thr Gly Ser Ser Thr Tyr Tyr Ala Asp Ser
1               5                   10                  15

Val Lys Gly Arg Phe
          20

<210> SEQ ID NO 17
<211> LENGTH: 21
<212> TYPE: PRT
<213> ORGANISM: Artificial
<220> FEATURE:
<223> OTHER INFORMATION: Synthetic Construct

<400> SEQUENCE: 17

Val Ser Ser Ile Ser Gly Ser Gly Ser Thr Thr Tyr Tyr Ala Asp Ser
1               5                   10                  15

Val Lys Gly Arg Phe
          20

<210> SEQ ID NO 18
<211> LENGTH: 21
<212> TYPE: PRT
<213> ORGANISM: Artificial
<220> FEATURE:
<223> OTHER INFORMATION: Synthetic Construct

<400> SEQUENCE: 18

Val Ser Val Ile Ser Gly Tyr Gly Ser Ser Thr Tyr Tyr Ala Asp Ser
```

```
1               5               10              15

Val Lys Gly Arg Phe
                20

<210> SEQ ID NO 19
<211> LENGTH: 21
<212> TYPE: PRT
<213> ORGANISM: Artificial
<220> FEATURE:
<223> OTHER INFORMATION: Synthetic Construct

<400> SEQUENCE: 19

Val Ser Val Ile Ser Gly Ala Gly Ser Ser Thr Tyr Tyr Ala Asp Ser
1               5               10              15

Val Lys Gly Arg Phe
                20

<210> SEQ ID NO 20
<211> LENGTH: 21
<212> TYPE: PRT
<213> ORGANISM: Artificial
<220> FEATURE:
<223> OTHER INFORMATION: Synthetic Construct

<400> SEQUENCE: 20

Val Ser Val Ile Ser Gly Tyr Gly Ser Thr Thr Tyr Tyr Ala Asp Ser
1               5               10              15

Val Lys Gly Arg Phe
                20

<210> SEQ ID NO 21
<211> LENGTH: 11
<212> TYPE: PRT
<213> ORGANISM: Artificial
<220> FEATURE:
<223> OTHER INFORMATION: Synthetic Construct

<400> SEQUENCE: 21

Ala Arg Asp Pro Gly Val Gly Gly Phe Asp Val
1               5               10

<210> SEQ ID NO 22
<211> LENGTH: 11
<212> TYPE: PRT
<213> ORGANISM: Artificial
<220> FEATURE:
<223> OTHER INFORMATION: Synthetic Construct

<400> SEQUENCE: 22

Ala Arg Ala Ser Ser Tyr Gly Gly Phe Asp Tyr
1               5               10

<210> SEQ ID NO 23
<211> LENGTH: 10
<212> TYPE: PRT
<213> ORGANISM: Artificial
<220> FEATURE:
<223> OTHER INFORMATION: Synthetic Construct

<400> SEQUENCE: 23

Ala Arg Gly Ala Tyr Gly Tyr Phe Asp Tyr
1               5               10

<210> SEQ ID NO 24
<211> LENGTH: 12
```

```
<212> TYPE: PRT
<213> ORGANISM: Artificial
<220> FEATURE:
<223> OTHER INFORMATION: Synthetic Construct

<400> SEQUENCE: 24

Ala Arg Ser Gly Gly Gly Gly Tyr Tyr Phe Asp Tyr
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic Construct

<400> SEQUENCE: 25

Ala Arg Arg Gly Leu Thr Ser Thr Tyr Phe Asp Tyr
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic Construct

<400> SEQUENCE: 26

Ala Arg His Ser His Ser Arg Tyr Ala Phe Asp Tyr
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic Construct

<400> SEQUENCE: 27

Ala Arg Gly Ser Tyr Tyr Gly Ala Gly Ser Phe Asp Tyr
1               5                   10

<210> SEQ ID NO 28
<211> LENGTH: 12
<212> TYPE: PRT
<213> ORGANISM: Artificial
<220> FEATURE:
<223> OTHER INFORMATION: Synthetic Construct

<400> SEQUENCE: 28

Ala Arg Gly Ser Tyr Ser Ser Val Tyr Phe Asp Val
1               5                   10

<210> SEQ ID NO 29
<211> LENGTH: 12
<212> TYPE: PRT
<213> ORGANISM: Artificial
<220> FEATURE:
<223> OTHER INFORMATION: Synthetic Construct

<400> SEQUENCE: 29

Ala Arg Arg Thr Pro Ala Gly Asn Tyr Phe Asp Tyr
1               5                   10

<210> SEQ ID NO 30
<211> LENGTH: 11
<212> TYPE: PRT
```

<213> ORGANISM: Artificial
<220> FEATURE:
<223> OTHER INFORMATION: Synthetic Construct

<400> SEQUENCE: 30

Ala Arg Ser Thr Val Ala Thr Pro Phe Ala Tyr
1               5                   10

<210> SEQ ID NO 31
<211> LENGTH: 12
<212> TYPE: PRT
<213> ORGANISM: Artificial
<220> FEATURE:
<223> OTHER INFORMATION: Synthetic Construct

<400> SEQUENCE: 31

Arg Ala Ser Gln Ser Val Arg Arg Arg Phe Leu Ala
1               5                   10

<210> SEQ ID NO 32
<211> LENGTH: 11
<212> TYPE: PRT
<213> ORGANISM: Artificial
<220> FEATURE:
<223> OTHER INFORMATION: Synthetic Construct

<400> SEQUENCE: 32

Arg Ala Ser Gln Asp Val Ser Thr Ala Val Ala
1               5                   10

<210> SEQ ID NO 33
<211> LENGTH: 10
<212> TYPE: PRT
<213> ORGANISM: Artificial
<220> FEATURE:
<223> OTHER INFORMATION: Synthetic Construct

<400> SEQUENCE: 33

Pro Ala Ser Ser Ser Val Ser Tyr Ile His
1               5                   10

<210> SEQ ID NO 34
<211> LENGTH: 11
<212> TYPE: PRT
<213> ORGANISM: Artificial
<220> FEATURE:
<223> OTHER INFORMATION: Synthetic Construct

<400> SEQUENCE: 34

Arg Ala Ser Gln Gly Ile Arg Ser Tyr Leu Ala
1               5                   10

<210> SEQ ID NO 35
<211> LENGTH: 11
<212> TYPE: PRT
<213> ORGANISM: Artificial
<220> FEATURE:
<223> OTHER INFORMATION: Synthetic Construct

<400> SEQUENCE: 35

Arg Ala Ser Gln Ser Val Gly Ser Trp Leu Ala
1               5                   10

<210> SEQ ID NO 36
<211> LENGTH: 10
<212> TYPE: PRT
<213> ORGANISM: Artificial

-continued

```
<220> FEATURE:
<223> OTHER INFORMATION: Synthetic Construct

<400> SEQUENCE: 36

Arg Ala Ser His Val Arg Thr Ala Val Ala
1               5                   10

<210> SEQ ID NO 37
<211> LENGTH: 11
<212> TYPE: PRT
<213> ORGANISM: Artificial
<220> FEATURE:
<223> OTHER INFORMATION: Synthetic Construct

<400> SEQUENCE: 37

Arg Ala Ser Gln Gly Ile Thr Ser Ala Leu Ala
1               5                   10

<210> SEQ ID NO 38
<211> LENGTH: 11
<212> TYPE: PRT
<213> ORGANISM: Artificial
<220> FEATURE:
<223> OTHER INFORMATION: Synthetic Construct

<400> SEQUENCE: 38

Lys Ala Ser Gln Asp Val Arg Thr Ala Val Ala
1               5                   10

<210> SEQ ID NO 39
<211> LENGTH: 11
<212> TYPE: PRT
<213> ORGANISM: Artificial
<220> FEATURE:
<223> OTHER INFORMATION: Synthetic Construct

<400> SEQUENCE: 39

Arg Ala Ser Gln Gly Ile Ser Arg Trp Leu Ala
1               5                   10

<210> SEQ ID NO 40
<211> LENGTH: 11
<212> TYPE: PRT
<213> ORGANISM: Artificial
<220> FEATURE:
<223> OTHER INFORMATION: Synthetic Construct

<400> SEQUENCE: 40

Lys Ala Ser Gln Asp Val Arg Thr Ala Val Ala
1               5                   10

<210> SEQ ID NO 41
<211> LENGTH: 9
<212> TYPE: PRT
<213> ORGANISM: Artificial
<220> FEATURE:
<223> OTHER INFORMATION: Synthetic Construct

<400> SEQUENCE: 41

Asp Ala Ser Ser Leu Glu Ser Gly Val
1               5

<210> SEQ ID NO 42
<211> LENGTH: 9
<212> TYPE: PRT
<213> ORGANISM: Artificial
<220> FEATURE:
```

-continued

```
<223> OTHER INFORMATION: Synthetic Construct

<400> SEQUENCE: 42

Asp Ala Ser Asn Arg Ala Thr Gly Ile
1               5

<210> SEQ ID NO 43
<211> LENGTH: 9
<212> TYPE: PRT
<213> ORGANISM: Artificial
<220> FEATURE:
<223> OTHER INFORMATION: Synthetic Construct

<400> SEQUENCE: 43

Asp Ala Ser Asn Leu Glu Thr Gly Val
1               5

<210> SEQ ID NO 44
<211> LENGTH: 9
<212> TYPE: PRT
<213> ORGANISM: Artificial
<220> FEATURE:
<223> OTHER INFORMATION: Synthetic Construct

<400> SEQUENCE: 44

Ala Ala Ser Ser Leu Gln Ser Gly Val
1               5

<210> SEQ ID NO 45
<211> LENGTH: 9
<212> TYPE: PRT
<213> ORGANISM: Artificial
<220> FEATURE:
<223> OTHER INFORMATION: Synthetic Construct

<400> SEQUENCE: 45

Asp Ala Ser Asn Leu Glu Thr Gly Val
1               5

<210> SEQ ID NO 46
<211> LENGTH: 9
<212> TYPE: PRT
<213> ORGANISM: Artificial
<220> FEATURE:
<223> OTHER INFORMATION: Synthetic Construct

<400> SEQUENCE: 46

Asp Ala Ser Asn Leu Glu Thr Gly Val
1               5

<210> SEQ ID NO 47
<211> LENGTH: 9
<212> TYPE: PRT
<213> ORGANISM: Artificial
<220> FEATURE:
<223> OTHER INFORMATION: Synthetic Construct

<400> SEQUENCE: 47

Asp Ala Ser Ser Leu Glu Ser Gly Val
1               5

<210> SEQ ID NO 48
<211> LENGTH: 9
<212> TYPE: PRT
<213> ORGANISM: Artificial
<220> FEATURE:
<223> OTHER INFORMATION: Synthetic Construct
```

<400> SEQUENCE: 48

Ala Ala Ser Ser Leu Gln Ser Gly Val
1               5

<210> SEQ ID NO 49
<211> LENGTH: 9
<212> TYPE: PRT
<213> ORGANISM: Artificial
<220> FEATURE:
<223> OTHER INFORMATION: Synthetic Construct

<400> SEQUENCE: 49

Asp Ala Ser Ser Leu Glu Ser Gly Val
1               5

<210> SEQ ID NO 50
<211> LENGTH: 9
<212> TYPE: PRT
<213> ORGANISM: Artificial
<220> FEATURE:
<223> OTHER INFORMATION: Synthetic Construct

<400> SEQUENCE: 50

Ala Ala Ser Thr Leu Gln Ser Gly Val
1               5

<210> SEQ ID NO 51
<211> LENGTH: 11
<212> TYPE: PRT
<213> ORGANISM: Artificial
<220> FEATURE:
<223> OTHER INFORMATION: Synthetic Construct

<400> SEQUENCE: 51

Tyr Cys Gln Gln Tyr Tyr Pro Ile Pro Arg Thr
1               5                   10

<210> SEQ ID NO 52
<211> LENGTH: 11
<212> TYPE: PRT
<213> ORGANISM: Artificial
<220> FEATURE:
<223> OTHER INFORMATION: Synthetic Construct

<400> SEQUENCE: 52

Tyr Cys Gln Gln Tyr Tyr Pro Trp Pro Trp Thr
1               5                   10

<210> SEQ ID NO 53
<211> LENGTH: 11
<212> TYPE: PRT
<213> ORGANISM: Artificial
<220> FEATURE:
<223> OTHER INFORMATION: Synthetic Construct

<400> SEQUENCE: 53

Tyr Cys Gln Gln Tyr Tyr Pro Trp Pro Trp Thr
1               5                   10

<210> SEQ ID NO 54
<211> LENGTH: 11
<212> TYPE: PRT
<213> ORGANISM: Artificial
<220> FEATURE:
<223> OTHER INFORMATION: Synthetic Construct -continued

```
<400> SEQUENCE: 54

Tyr Cys Gln Gln Ser Tyr His Trp Pro Leu Thr
1               5                   10

<210> SEQ ID NO 55
<211> LENGTH: 11
<212> TYPE: PRT
<213> ORGANISM: Artificial
<220> FEATURE:
<223> OTHER INFORMATION: Synthetic Construct

<400> SEQUENCE: 55

Tyr Cys Gln Gln Ser Tyr Pro Ile Pro Pro Thr
1               5                   10

<210> SEQ ID NO 56
<211> LENGTH: 11
<212> TYPE: PRT
<213> ORGANISM: Artificial
<220> FEATURE:
<223> OTHER INFORMATION: Synthetic Construct

<400> SEQUENCE: 56

Tyr Cys Gln Gln Tyr Tyr Pro Trp Pro Trp Thr
1               5                   10

<210> SEQ ID NO 57
<211> LENGTH: 11
<212> TYPE: PRT
<213> ORGANISM: Artificial
<220> FEATURE:
<223> OTHER INFORMATION: Synthetic Construct

<400> SEQUENCE: 57

Tyr Cys Gln Gln Tyr Tyr Pro Trp Pro Trp Thr
1               5                   10

<210> SEQ ID NO 58
<211> LENGTH: 11
<212> TYPE: PRT
<213> ORGANISM: Artificial
<220> FEATURE:
<223> OTHER INFORMATION: Synthetic Construct

<400> SEQUENCE: 58

Tyr Cys Gln Gln Ser Tyr Pro Ile Pro Phe Thr
1               5                   10

<210> SEQ ID NO 59
<211> LENGTH: 11
<212> TYPE: PRT
<213> ORGANISM: Artificial
<220> FEATURE:
<223> OTHER INFORMATION: Synthetic Construct

<400> SEQUENCE: 59

Tyr Cys Glu Gln Tyr Leu Glu Val Pro Pro Thr
1               5                   10

<210> SEQ ID NO 60
<211> LENGTH: 11
<212> TYPE: PRT
<213> ORGANISM: Artificial
<220> FEATURE:
<223> OTHER INFORMATION: Synthetic Construct

<400> SEQUENCE: 60
```

-continued

```
Tyr Cys Gln Gln Ser Tyr Pro Trp Pro Trp Thr
1               5                   10

<210> SEQ ID NO 61
<211> LENGTH: 118
<212> TYPE: PRT
<213> ORGANISM: Artificial
<220> FEATURE:
<223> OTHER INFORMATION: Synthetic Construct

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Val
        35                  40                  45

Ser Val Ile Ser Gly Tyr Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Asp Pro Gly Val Gly Gly Phe Asp Val Trp Gly Gln Gly Thr
                100                 105                 110

Leu Val Thr Val Ser Ser
            115

<210> SEQ ID NO 62
<211> LENGTH: 118
<212> TYPE: PRT
<213> ORGANISM: Artificial
<220> FEATURE:
<223> OTHER INFORMATION: Synthetic Construct

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Ala Ile His Trp Val Arg Gln Ala Pro Gly Lys Gly Leu Glu Trp Val
        35                  40                  45

Ser Val Ile Ser Gly Tyr Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ala Ser Ser Tyr Gly Gly Phe Asp Tyr Trp Gly Gln Gly Thr
                100                 105                 110

Leu Val Thr Val Ser Ser
            115

<210> SEQ ID NO 63
<211> LENGTH: 118
<212> TYPE: PRT
<213> ORGANISM: Artificial
<220> FEATURE:
<223> OTHER INFORMATION: Synthetic Construct
```

-continued

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr Tyr Trp Gly Trp Ile Arg Gln Ala Pro Gly Lys Gly Leu Glu Trp
        35                  40                  45

Val Ser Ser Ile Ser Gly Tyr Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Ala Tyr Gly Tyr Phe Asp Tyr Trp Gly Gln Gly Thr
            100                 105                 110

Leu Val Thr Val Ser Ser
        115

<210> SEQ ID NO 64
<211> LENGTH: 119
<212> TYPE: PRT
<213> ORGANISM: Artificial
<220> FEATURE:
<223> OTHER INFORMATION: Synthetic Construct

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Val
        35                  40                  45

Ser Val Ile Ser Gly Tyr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Gly Gly Gly Gly Tyr Tyr Phe Asp Tyr Trp Gly Gln Gly
            100                 105                 110

Thr Leu Val Thr Val Ser Ser
        115

<210> SEQ ID NO 65
<211> LENGTH: 119
<212> TYPE: PRT
<213> ORGANISM: Artificial
<220> FEATURE:
<223> OTHER INFORMATION: Synthetic Construct

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

-continued

```
Ser Val Ile Ser Gly Tyr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Arg Gly Leu Thr Ser Thr Tyr Phe Asp Tyr Trp Gly Gln Gly
            100                 105                 110

Thr Leu Val Thr Val Ser Ser
        115

<210> SEQ ID NO 66
<211> LENGTH: 119
<212> TYPE: PRT
<213> ORGANISM: Artificial
<220> FEATURE:
<223> OTHER INFORMATION: Synthetic Construct

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asn Tyr
                20                  25                  30

Ala Ile His Trp Val Arg Gln Ala Pro Gly Lys Gly Leu Glu Trp Val
            35                  40                  45

Ser Ala Ile Ser Gly Thr Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg His Ser His Ser Arg Tyr Ala Phe Asp Tyr Trp Gly Gln Gly
            100                 105                 110

Thr Leu Val Thr Val Ser Ser
        115

<210> SEQ ID NO 67
<211> LENGTH: 121
<212> TYPE: PRT
<213> ORGANISM: Artificial
<220> FEATURE:
<223> OTHER INFORMATION: Synthetic Construct

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
                20                  25                  30

His His Trp Ala Trp Ile Arg Gln Ala Pro Gly Lys Gly Leu Glu Trp
            35                  40                  45

Val Ser Ser Ile Ser Gly Ser Gly Ser Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Ser Tyr Tyr Gly Ala Gly Ser Phe Asp Tyr Trp Gly
```

-continued

```
                100                 105                 110

Gln Gly Thr Leu Val Thr Val Ser Ser
        115                 120

<210> SEQ ID NO 68
<211> LENGTH: 119
<212> TYPE: PRT
<213> ORGANISM: Artificial
<220> FEATURE:
<223> OTHER INFORMATION: Synthetic Construct

<400> SEQUENCE: 68

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Thr Asp Tyr
            20                  25                  30

Ala Ile His Trp Val Arg Gln Ala Pro Gly Lys Gly Leu Glu Trp Val
            35                  40                  45

Ser Val Ile Ser Gly Tyr Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Ser Tyr Ser Ser Val Tyr Phe Asp Val Trp Gly Gln Gly
            100                 105                 110

Thr Leu Val Thr Val Ser Ser
        115

<210> SEQ ID NO 69
<211> LENGTH: 119
<212> TYPE: PRT
<213> ORGANISM: Artificial
<220> FEATURE:
<223> OTHER INFORMATION: Synthetic Construct

<400> SEQUENCE: 69

Glu Val Gln Leu Val Glu Ser Gly Gly Gly Leu Val Gln Pro Gly Gly
1                   5                   10                  15

Ser Leu Arg Leu Ser Cys Ala Ala Ser Gly Tyr Thr Phe Ser Ser Tyr
            20                  25                  30

Ala Ile His Trp Val Arg Gln Ala Pro Gly Lys Gly Leu Glu Trp Val
            35                  40                  45

Ser Val Ile Ser Gly Ala Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Arg Thr Pro Ala Gly Asn Tyr Phe Asp Tyr Trp Gly Gln Gly
            100                 105                 110

Thr Leu Val Thr Val Ser Ser
        115

<210> SEQ ID NO 70
<211> LENGTH: 118
<212> TYPE: PRT
<213> ORGANISM: Artificial
<220> FEATURE:
```

<223> OTHER INFORMATION: Synthetic Construct

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Ile His Trp Val Arg Gln Ala Pro Gly Lys Gly Leu Glu Trp Val
        35                  40                  45

Ser Val Ile Ser Gly Tyr Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Thr Val Ala Thr Pro Phe Ala Tyr Trp Gly Gln Gly Thr
            100                 105                 110

Leu Val Thr Val Ser Ser
        115
```

<210> SEQ ID NO 71
<211> LENGTH: 108
<212> TYPE: PRT
<213> ORGANISM: Artificial
<220> FEATURE:
<223> OTHER INFORMATION: Synthetic Construct

<400> SEQUENCE: 71

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Arg Arg Arg
            20                  25                  30

Phe Leu Ala Trp Tyr Gln Gln Lys Pro Gly Lys Ala Pro Lys Leu Leu
        35                  40                  45

Ile Tyr Asp Ala Ser Ser Leu Glu Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Tyr Pro Ile Pro
                85                  90                  95

Arg Thr Phe Gly Gln Gly Thr Lys Val Glu Ile Lys
            100                 105
```

<210> SEQ ID NO 72
<211> LENGTH: 107
<212> TYPE: PRT
<213> ORGANISM: Artificial
<220> FEATURE:
<223> OTHER INFORMATION: Synthetic Construct

<400> SEQUENCE: 72

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
```

```
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Pro Trp Pro Trp
                    85                  90                  95

Thr Phe Gly Gln Gly Thr Lys Val Glu Ile Lys
            100                 105
```

```
<210> SEQ ID NO 73
<211> LENGTH: 106
<212> TYPE: PRT
<213> ORGANISM: Artificial
<220> FEATURE:
<223> OTHER INFORMATION: Synthetic Construct

<400> SEQUENCE: 73

Asp Ile Gln Leu Thr Gln Ser Pro Ser Ser Leu Ser Ala Ser Val Gly
1               5                   10                  15

Asp Arg Val Thr Ile Thr Cys Pro Ala Ser Ser Ser Val Ser Tyr Ile
                20                  25                  30

His Trp Tyr Gln Gln Lys Pro Gly Lys Ala Pro Lys Leu Leu Ile Tyr
            35                  40                  45

Asp Ala Ser Asn Leu Glu Thr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr Tyr Pro Trp Pro Trp Thr
                85                  90                  95

Phe Gly Gln Gly Thr Lys Val Glu Ile Lys
            100                 105
```

```
<210> SEQ ID NO 74
<211> LENGTH: 107
<212> TYPE: PRT
<213> ORGANISM: Artificial
<220> FEATURE:
<223> OTHER INFORMATION: Synthetic Construct

<400> SEQUENCE: 74

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr His Trp Pro Leu
                85                  90                  95

Thr Phe Gly Gln Gly Thr Lys Val Glu Ile Lys
            100                 105
```

```
<210> SEQ ID NO 75
<211> LENGTH: 107
<212> TYPE: PRT
<213> ORGANISM: Artificial
<220> FEATURE:
```

-continued

```
<223> OTHER INFORMATION: Synthetic Construct

<400> SEQUENCE: 75

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ile Pro Pro
                85                  90                  95

Thr Phe Gly Gln Gly Thr Lys Val Glu Ile Lys
            100                 105

<210> SEQ ID NO 76
<211> LENGTH: 106
<212> TYPE: PRT
<213> ORGANISM: Artificial
<220> FEATURE:
<223> OTHER INFORMATION: Synthetic Construct

<400> SEQUENCE: 76

Asp Ile Gln Leu Thr Gln Ser Pro Ser Ser Leu Ser Ala Ser Val Gly
1               5                   10                  15

Asp Arg Val Thr Ile Thr Cys Arg Ala Ser His Val Arg Thr Ala Val
            20                  25                  30

Ala Trp Tyr Gln Gln Lys Pro Gly Lys Ala Pro Lys Leu Leu Ile Tyr
        35                  40                  45

Asp Ala Ser Asn Leu Glu Thr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr Tyr Pro Trp Pro Trp Thr
                85                  90                  95

Phe Gly Gln Gly Thr Lys Val Glu Ile Lys
            100                 105

<210> SEQ ID NO 77
<211> LENGTH: 107
<212> TYPE: PRT
<213> ORGANISM: Artificial
<220> FEATURE:
<223> OTHER INFORMATION: Synthetic Construct

<400> SEQUENCE: 77

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Thr Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65              70              75              80

Glu Asp Phe Ala Thr Tyr Tyr Cys Gln Gln Tyr Tyr Pro Trp Pro Trp
                85              90              95

Thr Phe Gly Gln Gly Thr Lys Val Glu Ile Lys
            100             105

<210> SEQ ID NO 78
<211> LENGTH: 107
<212> TYPE: PRT
<213> ORGANISM: Artificial
<220> FEATURE:
<223> OTHER INFORMATION: Synthetic Construct

<400> SEQUENCE: 78

Asp Ile Gln Leu Thr Gln Ser Pro Ser Ser Leu Ser Ala Ser Val Gly
1               5               10              15

Asp Arg Val Thr Ile Thr Cys Lys Ala Ser Gln Asp Val Arg Thr Ala
            20              25              30

Val Ala Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Pro Ile Pro Phe
                85              90              95

Thr Phe Gly Gln Gly Thr Lys Val Glu Ile Lys
            100             105

<210> SEQ ID NO 79
<211> LENGTH: 107
<212> TYPE: PRT
<213> ORGANISM: Artificial
<220> FEATURE:
<223> OTHER INFORMATION: Synthetic Construct

<400> SEQUENCE: 79

Asp Ile Gln Leu Thr Gln Ser Pro Ser Ser Leu Ser Ala Ser Val Gly
1               5               10              15

Asp Arg Val Thr Ile Thr Cys Arg Ala Ser Gln Gly Ile Ser Arg Trp
            20              25              30

Leu Ala Trp Tyr Gln Gln Lys Pro Gly Lys Ala Pro Lys Leu Leu Ile
        35              40              45

Tyr Asp Ala Ser Ser Leu Glu Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Glu Gln Tyr Leu Glu Val Pro Pro
                85              90              95

Thr Phe Gly Gln Gly Thr Lys Val Glu Ile Lys
            100             105

<210> SEQ ID NO 80
<211> LENGTH: 107
<212> TYPE: PRT
<213> ORGANISM: Artificial
<220> FEATURE:
<223> OTHER INFORMATION: Synthetic Construct

<400> SEQUENCE: 80
```

-continued

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Ala
                20                  25                  30

Val Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Trp Pro Trp
                85                  90                  95

Thr Phe Gly Gln Gly Thr Lys Val Glu Ile Lys
            100                 105

<210> SEQ ID NO 81
<211> LENGTH: 116
<212> TYPE: PRT
<213> ORGANISM: Artificial
<220> FEATURE:
<223> OTHER INFORMATION: Synthetic Construct

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Ala Gln Lys Leu Gln
        50                  55                  60

Gly Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 82
<211> LENGTH: 106
<212> TYPE: PRT
<213> ORGANISM: Artificial
<220> FEATURE:
<223> OTHER INFORMATION: Synthetic Construct

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
                20                  25                  30

Val Ser Trp Tyr Gln Gln Lys Pro Gly Lys Ala Pro Lys Leu Leu Ile
            35                  40                  45

Tyr Ala Ala Ser Asn Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
```

-continued

```
65              70              75              80

Glu Asp Phe Ala Thr Tyr Tyr Cys Gln Gln Ser Phe Ser Tyr Pro Thr
                85              90              95

Phe Gly Gln Gly Thr Lys Leu Glu Ile Lys
            100             105

<210> SEQ ID NO 83
<211> LENGTH: 122
<212> TYPE: PRT
<213> ORGANISM: Artificial
<220> FEATURE:
<223> OTHER INFORMATION: Synthetic Construct

<400> SEQUENCE: 83

Gln Val Gln Leu Val Gln Ser Gly Ala Glu Val Lys Lys Pro Gly Ser
1               5               10              15

Ser Val Lys Val Ser Cys Lys Ala Ser Gly Tyr Thr Phe Thr Asp Asn
            20              25              30

Tyr Met Ile Trp Val Arg Gln Ala Pro Gly Gln Gly Leu Glu Trp Met
        35              40              45

Gly Asp Ile Asn Pro Tyr Asn Gly Gly Thr Thr Phe Asn Gln Lys Phe
    50              55              60

Lys Gly Arg Val Thr Ile Thr Ala Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Glu Ser Pro Tyr Phe Ser Asn Leu Tyr Val Met Asp Tyr Trp
            100             105             110

Gly Gln Gly Thr Leu Val Thr Val Ser Ser
        115             120

<210> SEQ ID NO 84
<211> LENGTH: 111
<212> TYPE: PRT
<213> ORGANISM: Artificial
<220> FEATURE:
<223> OTHER INFORMATION: Synthetic Construct

<400> SEQUENCE: 84

Glu Ile Val Leu Thr Gln Ser Pro Ala Thr Leu Ser Leu Ser Pro Gly
1               5               10              15

Glu Arg Ala Thr Leu Ser Cys Lys Ala Ser Gln Ser Val Asp Tyr Asp
            20              25              30

Gly Asp Asn Tyr Met Asn Trp Tyr Gln Gln Lys Pro Gly Gln Ala Pro
        35              40              45

Arg Leu Leu Ile Tyr Ala Ala Ser Asn Leu Glu Ser Gly Ile Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys His Leu Ser Asn
                85              90              95

Glu Asp Leu Ser Thr Phe Gly Gly Gly Thr Lys Val Glu Ile Lys
            100             105             110

<210> SEQ ID NO 85
<211> LENGTH: 972
<212> TYPE: PRT
<213> ORGANISM: Homo sapiens
```

-continued

```
<400> SEQUENCE: 85

Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415
```

-continued

```
Leu Leu Cys Ala Ala Ser Gly Tyr Pro Gln Pro Asn Val Thr Trp Leu
        420             425             430

Gln Cys Ser Gly His Thr Asp Arg Cys Asp Glu Ala Gln Val Leu Gln
        435             440             445

Val Trp Asp Asp Pro Tyr Pro Glu Val Leu Ser Gln Glu Pro Phe His
        450             455             460

Lys Val Thr Val Gln Ser Leu Leu Thr Val Glu Thr Leu Glu His Asn
465             470             475             480

Gln Thr Tyr Glu Cys Arg Ala His Asn Ser Val Gly Ser Gly Ser Trp
                485             490             495

Ala Phe Ile Pro Ile Ser Ala Gly Ala His Thr His Pro Pro Asp Glu
                500             505             510

Phe Leu Phe Thr Pro Val Val Val Ala Cys Met Ser Ile Met Ala Leu
            515             520             525

Leu Leu Leu Leu Leu Leu Leu Leu Leu Tyr Lys Tyr Lys Gln Lys Pro
        530             535             540

Lys Tyr Gln Val Arg Trp Lys Ile Ile Glu Ser Tyr Glu Gly Asn Ser
545             550             555             560

Tyr Thr Phe Ile Asp Pro Thr Gln Leu Pro Tyr Asn Glu Lys Trp Glu
                565             570             575

Phe Pro Arg Asn Asn Leu Gln Phe Gly Lys Thr Leu Gly Ala Gly Ala
                580             585             590

Phe Gly Lys Val Val Glu Ala Thr Ala Phe Gly Leu Gly Lys Glu Asp
            595             600             605

Ala Val Leu Lys Val Ala Val Lys Met Leu Lys Ser Thr Ala His Ala
        610             615             620

Asp Glu Lys Glu Ala Leu Met Ser Glu Leu Lys Ile Met Ser His Leu
625             630             635             640

Gly Gln His Glu Asn Ile Val Asn Leu Leu Gly Ala Cys Thr His Gly
                645             650             655

Gly Pro Val Leu Val Ile Thr Glu Tyr Cys Cys Tyr Gly Asp Leu Leu
            660             665             670

Asn Phe Leu Arg Arg Lys Ala Glu Ala Met Leu Gly Pro Ser Leu Ser
        675             680             685

Pro Gly Gln Asp Pro Glu Gly Gly Val Asp Tyr Lys Asn Ile His Leu
        690             695             700

Glu Lys Lys Tyr Val Arg Arg Asp Ser Gly Phe Ser Ser Gln Gly Val
705             710             715             720

Asp Thr Tyr Val Glu Met Arg Pro Val Ser Thr Ser Ser Asn Asp Ser
                725             730             735

Phe Ser Glu Gln Asp Leu Asp Lys Glu Asp Gly Arg Pro Leu Glu Leu
                740             745             750

Arg Asp Leu Leu His Phe Ser Ser Gln Val Ala Gln Gly Met Ala Phe
        755             760             765

Leu Ala Ser Lys Asn Cys Ile His Arg Asp Val Ala Ala Arg Asn Val
        770             775             780

Leu Leu Thr Asn Gly His Val Ala Lys Ile Gly Asp Phe Gly Leu Ala
785             790             795             800

Arg Asp Ile Met Asn Asp Ser Asn Tyr Ile Val Lys Gly Asn Ala Arg
                805             810             815

Leu Pro Val Lys Trp Met Ala Pro Glu Ser Ile Phe Asp Cys Val Tyr
            820             825             830
```

-continued

```
Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
        850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
        930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 86
<211> LENGTH: 976
<212> TYPE: PRT
<213> ORGANISM: Macaca fascicularis

<400> SEQUENCE: 86

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
                20                  25                  30

Lys Pro Gly Glu Met Val Thr Leu Arg Cys Val Gly Asn Gly Ser Val
            35                  40                  45

Glu Trp Asp Gly Pro Ile Ser Pro His Trp Thr Leu Tyr Ser Asp Gly
        50                  55                  60

Pro Ser Ser Val Leu Thr Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Lys Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Leu Arg
        130                 135                 140

Gly Arg Pro Leu Leu Arg His Thr Asn Tyr Ser Phe Ser Pro Trp His
145                 150                 155                 160

Gly Phe Thr Ile His Arg Ala Lys Phe Ile Gln Gly Gln Asp Tyr Gln
                165                 170                 175

Cys Ser Ala Leu Met Gly Ser Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Glu Glu Leu Val Arg Ile Arg Gly Glu Ala Ala Gln Ile Val Cys
        210                 215                 220

Ser Ala Ser Asn Ile Asp Val Asp Phe Asp Val Phe Leu Gln His Asn
225                 230                 235                 240
```

```
Thr Thr Lys Leu Ala Ile Pro Gln Arg Ser Asp Phe His Asp Asn Arg
            245                 250                 255

Tyr Gln Lys Val Leu Thr Leu Ser Leu Gly Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asp Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Cys Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
            405                 410                 415

Leu Leu Cys Ala Ala Ser Gly Tyr Pro Gln Pro Asn Val Thr Trp Leu
            420                 425                 430

Gln Cys Ala Gly His Thr Asp Arg Cys Asp Glu Ala Gln Val Leu Gln
            435                 440                 445

Val Trp Val Asp Pro His Pro Glu Val Leu Ser Gln Glu Pro Phe Gln
    450                 455                 460

Lys Val Thr Val Gln Ser Leu Leu Thr Ala Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala Arg Thr His Pro Pro Asp Glu
            500                 505                 510

Phe Leu Phe Thr Pro Val Val Val Ala Cys Met Ser Val Met Ala Leu
            515                 520                 525

Leu Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
            565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
            645                 650                 655
```

-continued

```
Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Ala Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Trp Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
            770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
            850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Leu Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Ser Ser Ser
            930                 935                 940

Glu Pro Glu Glu Glu Ser Ser Ser Glu His Leu Ala Cys Cys Glu Gln
945                 950                 955                 960

Gly Asp Ile Ala Gln Pro Leu Leu Gln Pro Asn Asn Tyr Gln Phe Cys
                965                 970                 975
```

```
<210> SEQ ID NO 87
<211> LENGTH: 977
<212> TYPE: PRT
<213> ORGANISM: Mus musculus

<400> SEQUENCE: 87

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
            20                  25                  30

Glu Pro Gly Glu Thr Val Thr Leu Arg Cys Val Ser Asn Gly Ser Val
            35                  40                  45

Glu Trp Asp Gly Pro Ile Ser Pro Tyr Trp Thr Leu Asp Pro Glu Ser
            50                  55                  60
```

-continued

```
Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
                100                 105                 110

Gln Glu Val Thr Val Val Glu Gly Gln Glu Ala Val Leu Pro Cys Leu
            115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
                180                 185                 190

Leu Lys Val Asn Arg Val His Pro Glu Pro Pro Gln Ile Lys Leu Glu
            195                 200                 205

Pro Ser Lys Leu Val Arg Ile Arg Gly Glu Ala Ala Gln Ile Val Cys
    210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
                260                 265                 270

Ala Gly Ile Tyr Ser Cys Val Ala Ser Asn Asp Val Gly Thr Arg Thr
            275                 280                 285

Ala Thr Met Asn Phe Gln Val Val Glu Ser Ala Tyr Leu Asn Leu Thr
    290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
                340                 345                 350

Thr Gln Arg Ala Ile Tyr Arg Tyr Thr Phe Lys Leu Phe Leu Asn Arg
            355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
                420                 425                 430

Arg Gly His Thr Asp Arg Cys Asp Glu Ala Gln Ala Leu Gln Val Trp
            435                 440                 445

Asn Asp Thr His Pro Glu Val Leu Ser Gln Lys Pro Phe Asp Lys Val
    450                 455                 460

Ile Ile Gln Ser Gln Leu Pro Ile Gly Thr Leu Lys His Asn Met Thr
465                 470                 475                 480
```

-continued

```
Tyr Phe Cys Lys Thr His Asn Ser Val Gly Asn Ser Ser Gln Tyr Phe
            485                 490                 495

Arg Ala Val Ser Leu Gly Gln Ser Lys Gln Leu Pro Asp Glu Ser Leu
            500                 505                 510

Phe Thr Pro Val Val Val Ala Cys Met Ser Val Met Ser Leu Leu Val
            515                 520                 525

Leu Leu Leu Leu Leu Leu Leu Tyr Lys Tyr Lys Gln Lys Pro Lys Tyr
    530                 535                 540

Gln Val Arg Trp Lys Ile Ile Glu Arg Tyr Glu Gly Asn Ser Tyr Thr
545                 550                 555                 560

Phe Ile Asp Pro Thr Gln Leu Pro Tyr Asn Glu Lys Trp Glu Phe Pro
                565                 570                 575

Arg Asn Asn Leu Gln Phe Gly Lys Thr Leu Gly Ala Gly Ala Phe Gly
            580                 585                 590

Lys Val Val Glu Ala Thr Ala Phe Gly Leu Gly Lys Glu Asp Ala Val
            595                 600                 605

Leu Lys Val Ala Val Lys Met Leu Lys Ser Thr Ala His Ala Asp Glu
    610                 615                 620

Lys Glu Ala Leu Met Ser Glu Leu Lys Ile Met Ser His Leu Gly Gln
625                 630                 635                 640

His Glu Asn Ile Val Asn Leu Leu Gly Ala Cys Thr His Gly Gly Pro
                645                 650                 655

Val Leu Val Ile Thr Glu Tyr Cys Cys Tyr Gly Asp Leu Leu Asn Phe
                660                 665                 670

Leu Arg Arg Lys Ala Glu Ala Met Leu Gly Pro Ser Leu Ser Pro Gly
            675                 680                 685

Gln Asp Ser Glu Gly Asp Ser Ser Tyr Lys Asn Ile His Leu Glu Lys
            690                 695                 700

Lys Tyr Val Arg Arg Asp Ser Gly Phe Ser Ser Gln Gly Val Asp Thr
705                 710                 715                 720

Tyr Val Glu Met Arg Pro Val Ser Thr Ser Ser Ser Asp Ser Phe Phe
                725                 730                 735

Lys Gln Asp Leu Asp Lys Glu Ala Ser Arg Pro Leu Glu Leu Trp Asp
            740                 745                 750

Leu Leu His Phe Ser Ser Gln Val Ala Gln Gly Met Ala Phe Leu Ala
            755                 760                 765

Ser Lys Asn Cys Ile His Arg Asp Val Ala Ala Arg Asn Val Leu Leu
    770                 775                 780

Thr Ser Gly His Val Ala Lys Ile Gly Asp Phe Gly Leu Ala Arg Asp
785                 790                 795                 800

Ile Met Asn Asp Ser Asn Tyr Val Val Lys Gly Asn Ala Arg Leu Pro
                805                 810                 815

Val Lys Trp Met Ala Pro Glu Ser Ile Phe Asp Cys Val Tyr Thr Val
            820                 825                 830

Gln Ser Asp Val Trp Ser Tyr Gly Ile Leu Leu Trp Glu Ile Phe Ser
            835                 840                 845

Leu Gly Leu Asn Pro Tyr Pro Gly Ile Leu Val Asn Asn Lys Phe Tyr
    850                 855                 860

Lys Leu Val Lys Asp Gly Tyr Gln Met Ala Gln Pro Val Phe Ala Pro
865                 870                 875                 880

Lys Asn Ile Tyr Ser Ile Met Gln Ser Cys Trp Asp Leu Glu Pro Thr
                885                 890                 895

Arg Arg Pro Thr Phe Gln Gln Ile Cys Phe Leu Leu Gln Glu Gln Ala
```

-continued

```
              900                905                910

Arg Leu Glu Arg Arg Asp Gln Asp Tyr Ala Asn Leu Pro Ser Ser Gly
        915                920                925

Gly Ser Ser Gly Ser Asp Ser Gly Gly Gly Ser Ser Gly Gly Ser Ser
    930                935                940

Ser Glu Pro Glu Glu Glu Ser Ser Ser Glu His Leu Ala Cys Cys Glu
945                950                955                960

Pro Gly Asp Ile Ala Gln Pro Leu Leu Gln Pro Asn Asn Tyr Gln Phe
            965                970                975

Cys
```

ANTI-CSF1R MOLECULES AND USE THEREOF

FIELD OF THE INVENTION

The present disclosure relates to antibodies against human CSF-1R, methods for their production, pharmaceutical compositions containing said antibodies, and uses thereof.

SEQUENCE LISTING

A Sequence Listing accompanies this application and is submitted as an ASCII text file of the sequence listing named "177663_00004_ST25.txt" which is 63,997 bytes in size and was created on Jun. 20, 2022. The sequence listing is electronically submitted via EFS-Web with the application and is incorporated herein by reference in its entirety.

BACKGROUND

The CSF-1 receptor (CSF-1R; synonyms: M-CSF receptor; Macrophage colony-stimulating factor 1 receptor, EC 2.7.10.1, Fms proto-oncogene, c-fms, Swiss Prot P07333, CD115) is known since 1986 (Coussens, L. et al., Nature 320 (1986) 277-280). CSF-1R is a growth factor and encoded by the c-fms proto-oncogene (reviewed in Roth, P. and Stanley, E. R., Curr. Top. Microbiol. Immunol. 181 (1992) 141-67).

CSF-1R is the receptor for M-CSF (macrophage colony stimulating factor, also called CSF-1) and mediates the biological effects of this cytokine (Sherr, C. J. et al., Cell 41 (1985) 665-676). The cloning of the colony stimulating factor-1 receptor (also called c-fms) was described for the first time in Roussel, M. F. et al., Nature 325 (1987) 549-552. In that publication, it was shown that CSF-1R had transforming potential dependent on changes in the C-terminal tail of the protein including the loss of the inhibitory tyrosine 969 phosphorylation which binds Cb1 and thereby regulates receptor down regulation (Lee, P. S. et al., Embo J. 18 (1999) 3616-3628).

CSF-1R is a single chain, transmembrane receptor tyrosine kinase (RTK) and a member of the family of immunoglobulin (Ig) motif containing RTKs characterized by repeated Ig domains in the extracellular portion of the receptor. The intracellular protein tyrosine kinase domain is interrupted by a unique insert domain that is also present in the other related RTK class III family members that include the platelet derived growth factor receptors (PDGFR), stem cell growth factor receptor (c-Kit) and fms-like cytokine receptor (FLT3). In spite of the structural homology among this family of growth factor receptors, they have distinct tissue-specific functions. CSF-1R is mainly expressed on cells of the monocytic lineage and in the female reproductive tract and placenta. In addition expression of CSF-1R has been reported in Langerhans cells in skin, a subset of smooth muscle cells (Inaba, T. et al., J. Biol. Chem. 267 (1992) 5693-5699), B cells (Baker, A. H. et al., Oncogene 8 (1993) 371-378) and microglia (Sawada, M. et al., Brain Res. 509 (1990) 119-124).

The main biological effects of CSF-1R signaling are the differentiation, proliferation, migration, and survival of hematopoietic precursor cells to the macrophage lineage (including osteoclast). Activation of CSF-1R is mediated by its ligand, M-CSF. Binding of M-CSF to CSF-1R induces the formation of homodimers and activation of the kinase by tyrosine phosphorylation (Stanley, E. R. et al., Mol. Reprod. Dev. 46 (1997) 4-10). Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCy, and Cb1 (Bourette, R. P. and Rohrschneider, L. R., Growth Factors 17 (2000) 155-166).

CSF-1R signaling has a physiological role in immune responses, in bone remodeling and in the reproductive system. The knockout animals for either M-CSF-1 (Pollard, J. W., Mol. Reprod. Dev. 46 (1997) 54-61) or CSF-1R (Dai, X. M. et al., Blood 99 (2002) 111-120) have been shown to have osteopetrotic, hematopoietic, tissue macrophage, and reproductive phenotypes consistent with a role for CSF-1R in the respective cell types.

SUMMARY OF THE INVENTION

The invention, in one aspect, provides an isolated monoclonal antibody or an antigen-binding fragment thereof, which specifically binds to human CSF-1R.

The invention, in another aspect, provides an isolated monoclonal antibody or an antigen-binding fragment thereof, which comprises (1) a heavy chain variable domain (VH) comprising a complementary determining region (CDR) 1 as set forth in SEQ ID NO: 1, a CDR2 as set forth in SEQ ID NO: 11 and a CDR3 as set forth in SEQ ID NO: 21, and a light chain variable domain (VL) comprising a CDR1 as set forth in SEQ ID NO: 31, a CDR2 as set forth in SEQ ID NO: 41 and a CDR3 as set forth in SEQ ID NO: 51;

(2) a VH comprising a CDR1 as set forth in SEQ ID NO: 2, a CDR2 as set forth in SEQ ID NO: 12 and a CDR3 as set forth in SEQ ID NO: 22, and a VL comprising a CDR1 as set forth in SEQ ID NO: 32, a CDR2 as set forth in SEQ ID NO: 42 and a CDR3 as set forth in SEQ ID NO: 52;

(3) a VH comprising a CDR1 as set forth in SEQ ID NO: 3, a CDR2 as set forth in SEQ ID NO: 13 and a CDR3 as set forth in SEQ ID NO: 23, and a VL comprising a CDR1 as set forth in SEQ ID NO: 33, a CDR2 as set forth in SEQ ID NO: 43 and a CDR3 as set forth in SEQ ID NO: 53;

(4) a VH comprising a CDR1 as set forth in SEQ ID NO: 4, a CDR2 as set forth in SEQ ID NO: 14 and a CDR3 as set forth in SEQ ID NO: 24, and a VL comprising a CDR1 as set forth in SEQ ID NO: 34, a CDR2 as set forth in SEQ ID NO: 44 and a CDR3 as set forth in SEQ ID NO: 54;

(5) a VH comprising a CDR1 as set forth in SEQ ID NO: 5, a CDR2 as set forth in SEQ ID NO: 15 and a CDR3 as set forth in SEQ ID NO: 25, and a VL comprising a CDR1 as set forth in SEQ ID NO: 35, a CDR2 as set forth in SEQ ID NO: 45 and a CDR3 as set forth in SEQ ID NO: 55;

(6) a VH comprising a CDR1 as set forth in SEQ ID NO: 6, a CDR2 as set forth in SEQ ID NO: 16 and a CDR3 as set forth in SEQ ID NO: 26, and a VL comprising a CDR1 as set forth in SEQ ID NO: 36, a CDR2 as set forth in SEQ ID NO: 46 and a CDR3 as set forth in SEQ ID NO: 56;

(7) a VH comprising a CDR1 as set forth in SEQ ID NO: 7, a CDR2 as set forth in SEQ ID NO: 17 and a CDR3 as set forth in SEQ ID NO: 27, and a VL comprising a CDR1 as set forth in SEQ ID NO: 37, a CDR2 as set forth in SEQ ID NO: 47 and a CDR3 as set forth in SEQ ID NO: 57;

(8) a VH comprising a CDR1 as set forth in SEQ ID NO: 8, a CDR2 as set forth in SEQ ID NO: 18 and a CDR3 as set forth in SEQ ID NO: 28, and a VL comprising a CDR1 as set forth in SEQ ID NO: 38, a CDR2 as set forth in SEQ ID NO: 48 and a CDR3 as set forth in SEQ ID NO: 58;

(9) a VH comprising a CDR1 as set forth in SEQ ID NO: 9, a CDR2 as set forth in SEQ ID NO: 19 and a CDR3 as set forth in SEQ ID NO: 29, and a VL comprising a CDR1 as set forth in SEQ ID NO: 39, a CDR2 as set forth in SEQ ID NO: 49 and a CDR3 as set forth in SEQ ID NO: 59; or

(10) a VH comprising a CDR1 as set forth in SEQ ID NO: 10, a CDR2 as set forth in SEQ ID NO: 20 and a CDR3 as set forth in SEQ ID NO: 30, and a VL comprising a CDR1 as set forth in SEQ ID NO: 40, a CDR2 as set forth in SEQ ID NO: 50 and a CDR3 as set forth in SEQ ID NO: 60.

In one embodiment, the antibody or antigen-binding fragment of the invention comprises (1) a VH as set forth in SEQ ID NO: 61 and a VL as set forth in SEQ ID NO: 71;

(2) a VH as set forth in SEQ ID NO: 62 and a VL as set forth in SEQ ID NO: 72;

(3) a VH as set forth in SEQ ID NO: 63 and a VL as set forth in SEQ ID NO: 73;

(4) a VH as set forth in SEQ ID NO: 64 and a VL as set forth in SEQ ID NO: 74;

(5) a VH as set forth in SEQ ID NO: 65 and a VL as set forth in SEQ ID NO: 75;

(6) a VH as set forth in SEQ ID NO: 66 and a VL as set forth in SEQ ID NO: 76;

(7) a VH as set forth in SEQ ID NO: 67 and a VL as set forth in SEQ ID NO: 77;

(8) a VH as set forth in SEQ ID NO: 68 and a VL as set forth in SEQ ID NO: 78;

(9) a VH as set forth in SEQ ID NO: 69 and a VL as set forth in SEQ ID NO: 79; or

(10) a VH as set forth in SEQ ID NO: 70 and a VL as set forth in SEQ ID NO: 80.

In one embodiment, the antibody or antigen-binding fragment comprising the above sequences specifically binds to human CSF-1R.

In one embodiment, the antibody or antigen-binding fragment of the invention is a full length antibody of the IgG1 or IgG4 subclass.

In one embodiment, the antibody or antigen-binding fragment of the invention is a full length antibody of the IgG4 subclass with the S241P mutation.

In one embodiment, the antibody or antigen-binding fragment of the invention is an antibody fragment selected from the group consisting of Fab, Fab', Fab-SH, F(ab)$_2$, scFv and diabody.

In one embodiment, the antibody or antigen-binding fragment of the invention possesses one or more of the following properties:

(1) having an affinity for human CSF-1R with $K_D$<40 nM, <35 nM, <30 nM, <25 nM, <20 nM, <15 nM, <10 nM, <9 nM, <8 nM, <7 nM, <6 nM, <5 nM, <4 nM, <3 nM, <2 nM, <1 nM, as determined by SPR using BIAcore;

(2) competing for binding to human CSF-1R with an antibody comprising a VH as set forth in SEQ ID NO: 81 and VL as set forth in SEQ ID NO: 82;

(3) binding to monkey CSF-1R;

(4) not binding to mouse CSF-1R;

(5) having a solubility higher than 80 mg/mL, higher than 90 mg/mL, higher than 100 mg/mL, higher than 110 mg/mL, higher than 120 mg/mL, higher than 130 mg/mL, or higher than 134 mg/mL, in a storage buffer, such as 20 mM histidine, pH 5.5, without obvious precipitation;

(6) having less than 10%, less than 9%, less than 8%, less than 7%, less than 6%, less than 5%, less than 4%, less than 3%, or less than 2% HMW at high concentration, and ΔHMW less than 1%, less than 0.9%, less than 0.8%, less than 0.7%, less than 0.6%, less than 0.5%, less than 0.4%, or less than 0.3% as compared with the 1 mg/ml solution in a storage buffer, such as 20 mM histidine, pH 5.5, as analyzed through SEC-HPLC;

(7) remaining stable after 6 cycles of freezing at −80° C. and thawing at room temperature in a storage buffer, such as 20 mM histidine, pH 5.5;

(8) remaining stable after 7 days at 50° C. in a storage buffer, such as 20 mM histidine, pH 5.5;

(9) inhibiting CSF-1R phosphorylation induced by CSF-1, particularly in a dose dependent manner, more particularly to an extent stronger than, similar to, or weaker than an antibody comprising a VH as set forth in SEQ ID NO: 81 and a VL as set forth in SEQ ID NO: 82;

(10) inhibiting CSF-1R phosphorylation induced by IL-34, particularly in a dose dependent manner, more particularly to an extent stronger than, similar to, or weaker than an antibody comprising a VH as set forth in SEQ ID NO: 81 and a VL as set forth in SEQ ID NO: 82;

(11) inhibiting monocyte proliferation induced by CSF-1, particularly in a dose dependent manner, more particularly to an extent stronger than, similar to, or weaker than an antibody comprising a VH as set forth in SEQ ID NO: 81 and a VL as set forth in SEQ ID NO: 82;

(12) inhibiting monocyte proliferation induced by IL-34, particularly in a dose dependent manner, more particularly to an extent stronger than, similar to, or weaker than an antibody comprising a VH as set forth in SEQ ID NO: 81 and a VL as set forth in SEQ ID NO: 82;

(13) having a mean $C_{max}$ greater than 200 μg/mL, greater than 210 μg/mL, greater than 220 μg/mL, greater than 230 μg/mL, greater than 240 μg/mL, or greater than 245 μg/mL, a mean $AUC_{0-864\,h}$ greater than 15000 μg·h/mL, greater than 16000 μg·h/mL, greater than 17000 μg·h/mL, greater than 18000 μg·h/mL, greater than 19000 μg·h/mL, or greater than 20000 μg·h/mL, and/or a mean tin greater than 50 hrs, greater than 60 hrs, greater than 70 hrs, greater than 80 hrs, greater than 90 hrs, or greater than 100 hrs at an i.v. dose of 10 mg/kg in the format of IgG1 in cynomolgus monkey;

(14) mediating rapid elimination of CD14$^+$CD16$^+$ monocytes in periphery blood at an i.v. dose of 10 mg/kg in the format of IgG1 in cynomolgus monkey, particularly by more than 70%, more than 80%, or more than 90%, particularly from day 1 to day 8 post-dose, from day 2 to day 8 post-dose, from day 3 to day 8 post-dose, from day 4 to day 8 post-dose, from day 1 to day 7 post-dose, from day 2 to day 7 post-dose, from day 3 to day 7 post-dose, from day 4 to day 7 post-dose, from day 1 to day 6 post-dose, from day 2 to day 6 post-dose, from day 3 to day 6 post-dose, from day 4 to day 6 post-dose, from day 1 to day 5 post-dose, from day 2 to day 5 post-dose, from day 3 to day 5 post-dose, from day 4 to day 5 post-dose, from day 1 to day 4 post-dose, from day 2 to day 4 post-dose, or from day 3 to day 4 post-dose; and/or

(15) mediating rapid increase of serum CSF-1 level at an i.v. dose of 10 mg/kg in the format of IgG1 in cynomolgus monkey; particularly as early as 8, 9, 10, 11, 12, 13, 14, 15, 16, 17, 18, 19, 20, 21, 22, or 23 hrs post-dose, or 1, 2, 3, or 4 days post-dose, particularly over 10-fold, over 20-fold, over 30-fold, over 40-fold, over 50-fold, over 60-fold, over 70 fold, over 80-fold, over 90-fold, over 100-fold, over 200-fold, over 300-fold, over 400-fold, over 500-fold, over 600-fold, over 700 fold, over 800-fold, over 900-fold, or over 1000-fold as compared to the pre-dose baseline, particularly from day 1 to day 16 post-dose, from day 1 to day 15 post-dose, from day 1 to day 14 post-dose, from day 1 to day 13 post-dose, from day 1 to day 12 post-dose, from day 1 to day 11 post-dose, from day 1 to day 10 post-dose, from day 1 to day 9 post-dose, from day 1 to day 8 post-dose, from day 2 to day 16 post-dose, from day 2 to day 15 post-dose, from day 2 to day 14 post-dose, from day 2 to day 13 post-dose, from day 2 to day 12 post-dose, from day 2 to day 11 post-dose, from day 2 to day 10 post-dose, from day 2 to day 9 post-dose, from day 2 to day 8 post-dose, from day 3 to day 16 post-dose, from day 3 to day 15 post-dose, from day 3 to day 14 post-dose, from day 3 to day 13 post-dose, from day 3 to day 12 post-dose, from day 3 to day 11 post-dose, from day 3 to day 10 post-dose, from day 3 to day 9 post-dose, from day 3 to day 8 post-dose, from day 4 to day 16 post-dose, from day 4 to day 15 post-dose, from day 4 to day 14 post-dose, from day 4 to day 13 post-dose, from day 4 to day 12 post-dose, from day 4 to day 11 post-dose, from day 4 to day 10 post-dose, from day 4 to day 9 post-dose, from day 4 to day 8 post-dose, from day 5 to day 16 post-dose, from day 5 to day 15 post-dose, from day 5 to day 14 post-dose, from day 5 to day 13 post-dose, from day 5 to day 12 post-dose, from day 5 to day 11 post-dose, from day 5 to day 10 post-dose, from day 5 to day 9 post-dose, from day 5 to day 8 post-dose, from day 6 to day 16 post-dose, from day 6 to day 15 post-dose, from day 6 to day 14 post-dose, from day 6 to day 13 post-dose, from day 6 to day 12 post-dose, from day 6 to day 11 post-dose, from day 6 to day 10 post-dose, from day 6 to day 9 post-dose, from day 6 to day 8 post-dose, from day 1 to day 7 post-dose, from day 2 to day 6 post-dose, or from day 3 to day 5 post-dose, particularly lasting for 1, 2, 3, 4, 5, 6, 7, 8, 9, 10, 11, 12, 13, 14, 15, or 16 days.

The invention provides a pharmaceutical composition comprising the antibody or antigen-binding fragment of the invention.

The invention provides at least one polynucleotide encoding the antibody or antigen-binding fragment of the invention.

The invention provides at least one vector comprising the at least one polynucleotide of the invention.

The invention provides at least one host cell comprising the at least one or polynucleotide of the invention or the at least one vector of the invention.

The invention provides a method of producing the antibody or antigen-binding fragment of the invention, comprising culturing the at least one host cell of the invention under conditions suitable for the expression of the at least one polynucleotide of the invention and optionally recovering said antibody antigen-binding fragment.

The invention provides a method of treating disease, disorder, or condition in a subject comprising administrating a therapeutically effective amount of the antibody or antigen-binding fragment of the invention to the subject.

The invention provides use of the antibody or antigen-binding fragment of the invention in the manufacture of a medicament for the treatment of disease, disorder, or condition.

DETAILED DESCRIPTION OF THE INVENTION

Figure 1:
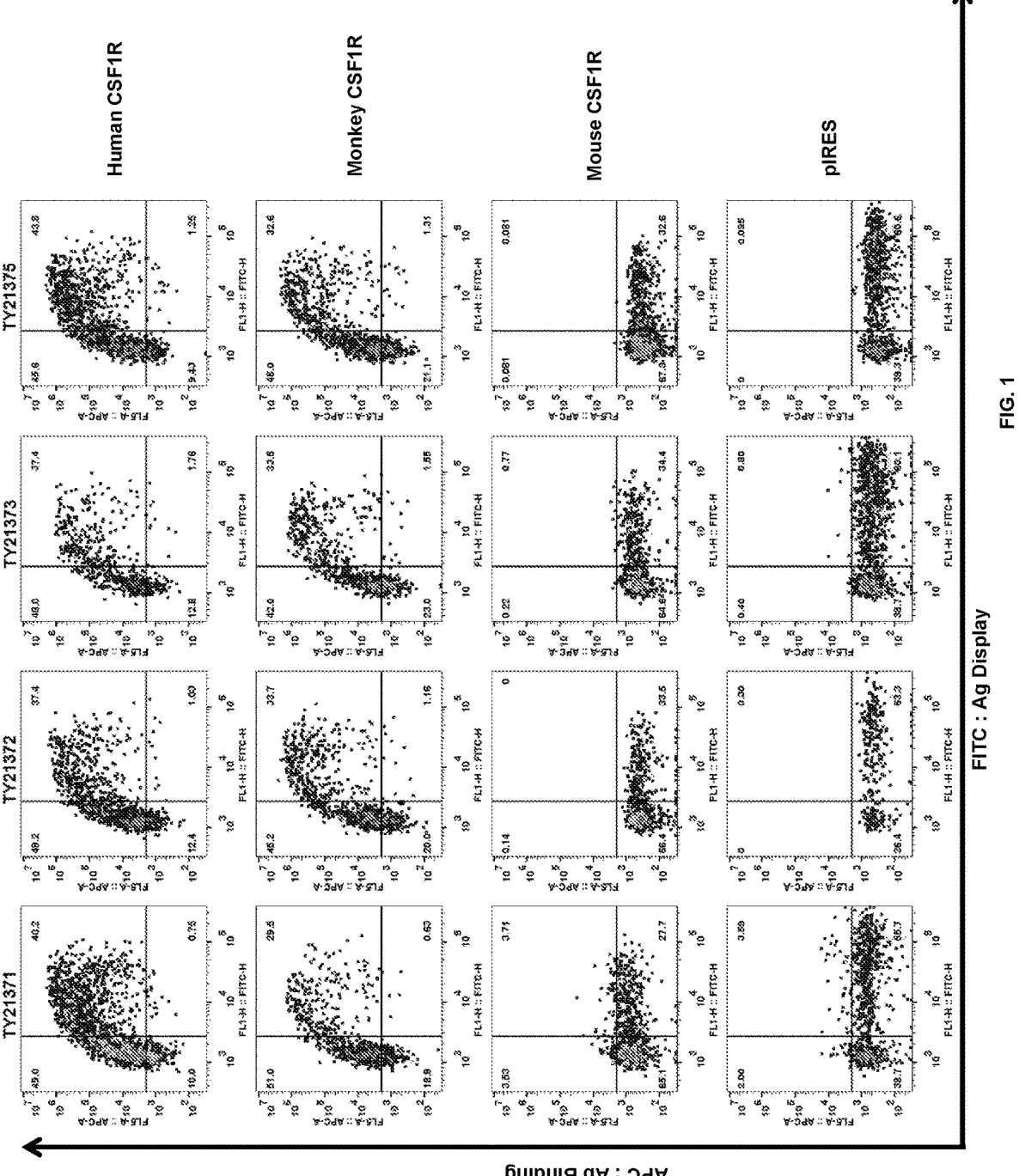
FIG. 1 shows the binding of the antibodies to human, monkey and mouse CSF-1R that are transiently expressed on the surface of HEK293F cells.

The term "antibody" encompasses the various forms of antibodies including but not being limited to whole antibodies, antibody fragments, humanized antibodies, chimeric antibodies, human antibody, T cell epitope depleted antibodies, and further genetically engineered antibodies as long as the characteristic properties according to the invention are retained.

"Antibody fragments" comprise a portion of a full length antibody, preferably the variable domain thereof, or at least the antigen binding site thereof. Examples of antibody fragments include Fab, Fab', Fab-SH, $F(ab')_2$, diabodies, single-chain antibody molecules (e.g., scFv), and multispecific antibodies formed from antibody fragments. scFv antibodies are, e.g., described in Houston, J. S., Methods in Enzymol. 203 (1991) 46-88). In addition, antibody fragments comprise single chain polypeptides having the characteristics of a $V_H$ domain binding to CSF-1R, namely being able to assemble together with a $V_L$ domain, or of a $V_L$ domain binding to CSF-1R, namely being able to assemble together with a $V_H$ domain to a functional antigen binding site and thereby providing the property.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "CDR-grafted variant" as used within the current application denotes a variable domain of an antibody comprising complementary determining regions (CDRs or hypervariable regions) from one source or species and framework regions (FRs) from a different source or species, usually prepared by recombinant DNA techniques. CDR-grafted variants of variable domains comprising murine CDRs and a human FRs are preferred.

The term "T-cell epitope depleted variant" as used within the current application denotes a variable domain of an antibody which was modified to remove or reduce immunogenicity by removing human T-cell epitopes (peptide sequences within the variable domains with the capacity to bind to MHC Class II molecules). By this method interactions between amino acid side chains of the variable domain and specific binding pockets with the MHC class II binding groove are identified. The identified immunogenic regions are mutated to eliminate immunogenicity. Such methods are described in general in, e.g., WO 98/52976.

The term "humanized variant" as used within the current application denotes a variable domain of an antibody, which is reconstituted from the complementarity determining regions (CDRs) of non-human origin, e.g. from a non-human species, and from the framework regions (FRs) of human origin, and which has been further modified in order to also reconstitute or improve the binding affinity and specifity of the original non-human variable domain. Such humanized variants are usually prepared by recombinant DNA techniques. The reconstitution of the affinity and specifity of the parent non-human variable domain is the critical step, for which different methods are currently used. In one method it is determined whether it is beneficial to introduce mutations, so called backmutations, in the non-human CDRs as well as in the human FRs. The suited positions for such backmutations can be identified e.g. by sequence or homology analysis, by choosing the human framework (fixed frameworks approach; homology matching or best-fit), by using consensus sequences, by selecting FRs from several different human mAbs, or by replacing non-human residues on the three dimensional surface with the most common residues found in human mAbs ("resurfacing" or "vencering").

The antibodies according to the invention include, in addition, such antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CSF-1R antibody can be preferably replaced with another amino acid residue from the same side chain family:

Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

The CSF-1 receptor (CSF-1R; synonyms: M-CSF receptor; Macrophage colony-stimulating factor 1 receptor, EC 2.7.10.1, Fms proto-oncogene, c-fms, Swiss Prot P07333, CD115) is known since 1986 (Coussens, L., et al., Nature 320 (1986) 277-280). CSF-1R is a growth factor and encoded by the c-fms proto-oncogene (reviewed e.g. in Roth, P., and Stanley, E. R., Curr. Top. Microbiol. Immunol. 181 (1992) 141-67).

CSF-1R is the receptor for M-CSF (macrophage colony stimulating factor, also called CSF-1) and mediates the biological effects of this cytokine (Sherr, C. J., et al., Cell 41 (1985) 665-676). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cb1 and thereby regulates receptor down regulation (Lee, P. S., et al., Embo J. 18 (1999) 3616-3628).

As used herein, "binding to human CSF-1R" refers to an antibody specifically binding to the human CSF-1R antigen. The binding affinity is of KD-value of $1.0 \times 10^{-8}$ mol/l or lower at 25° C., preferably of a KD-value of $1.0 \times 10^{-9}$ mol/l or lower at 25° C. The binding affinity is determined with a standard binding assay at 35° C., such as surface plasmon resonance technique (Biacore R.).

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents. Preferably an antibody according to the invention binds specifically to native but not to denatured CSF-1R.

The term "binding to the same epitope as the reference antibody" as used herein refers to an anti-CSF-1R antibody of the invention that binds to the same epitope on CSF-1R to which the reference antibody binds. The epitope binding property of an anti-CSF-1R antibody of the present invention may be determined using techniques known in the art. The CSF-1R antibody is measured at 25° C. by Surface Plasmon Resonance (SPR) in an in vitro competitive binding inhibition assay to determine the ability of the test antibody to inhibit binding of the reference antibody to CSF-1R. This can be investigated by a BIAcore assay (Pharmacia Biosensor AB, Uppsala, Sweden).

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding fragment" is an synonyms for the term "antigen-binding portion of an antibody". The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, MD (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy alpha-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

An embodiment of the invention is a method for the production of an antibody against human CSF-1R according to the invention characterized in that the sequence of a nucleic acid encoding the heavy chain of a human IgG1 class antibody binding to human CSF-1R and the nucleic acid encoding the light chain of said antibody are inserted into an expression vector, said vector is inserted in a eukaryotic host cell, the encoded protein is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Nucleic acid molecules encoding amino acid sequence variants of anti-CSF-1R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CSF-1R antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., eds. Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called $\alpha$, $\delta$, $\epsilon$, $\gamma$, and $\mu$, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743, Lukas, T. J., et al., J. Immunol. 127 (1981) 2555-2560, Brunhouse, R. and Cebra, J. J., Mol. Immunol. 16 (1979) 907-917, Burton et al., Nature 288 (1980) 338-344, Thommesen, J. E., et al., Mol. Immunol. 37 (2000) 995-1004, Idusogie, E. E., et al., J. Immunol. 164 (2000) 4178-4184, Hezarch, M., et al., J. Virology 75 (2001) 12161-12168, Morgan, A., et al., Immunology 86 (1995) 319-324, EP 0307434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P).

In one embodiment the antibody according to the invention is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218). It is further preferred that the antibody is of mouse origin and comprises the antibody variable sequence frame of a mouse antibody according to Kabat.

The invention comprises a method for the treatment of a patient in need of therapy, characterized by administering to the patient a therapeutically effective amount of an antibody according to the invention. The invention comprises the use of an antibody according to the invention for therapy.

Thus the antibodies according to the invention binding to the same epitope were able to inhibit cell proliferation in CSF-1 ligand-dependent and CSF-1 ligand independent cells. Especially the CSF-1R antibodies of the present invention are for use in the treatment of CSF-1 ligand-dependent and CSF-1 ligand-independent CSF-1R mediated diseases. This means that the CSF1-R mediated disease is either dependent of CSF-1 ligand and the corresponding signaling through CSF-1R and/or independent of CSF-1 ligand and the corresponding signaling through CSF-1R. Signaling through CSF-1R is likely involved in tumor growth and metastasis.

One embodiment of the invention are the CSF-1R antibodies of the present invention for use in the treatment of "CSF-1R mediated diseases" or the CSF-1R antibodies of the present invention for use for the manufacture of a medicament in the treatment of "CSF-1R mediated diseases".

The invention comprises the antibody characterized in comprising the antibody binding to human CSF-1R being characterized by the herein mentioned epitope binding properties or alternatively by the herein mentioned amino acid sequences and amino acid sequence fragments for treatment of a disease, disorder, or condition.

The invention comprises the use of an antibody characterized in comprising the antibody binding to human CSF-1R being characterized by the herein mentioned epitope binding properties or alternatively by the herein mentioned amino acid sequences and amino acid sequence fragments for treatment of a disease, disorder, or condition or alternatively for the manufacture of a medicament for the treatment of a disease, disorder, or condition.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/ resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from a disease, disorder, or condition.

The invention comprises also a method for the treatment of a patient suffering from a disease, disorder, or condition.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical composition, preferably together with a pharmaceutically acceptable carrier, for the treatment of a patient suffering from a disease, disorder, or condition.

Said disease, disorder, or condition is a CSF-1R mediated diseases, disorder, or condition.

The following examples and sequence listing are provided to aid the understanding of the present invention, the true scope of which is set forth in the appended claims. It is understood that modifications can be made in the procedures set forth without departing from the spirit of the invention.

| DESERIPTION OF THE SEQUENCES | | |
| --- | --- | --- |
| SEQ ID NO: | Description | Sequence |
| 1 | TY21371 HCDR1 | FTFSGYAIHWV |
| 2 | TY21372 HCDR1 | YTFSDYAIHWV |
| 3 | TY21373 HCDR1 | YSISSGYYWGWI |
| 4 | TY21375 HCDR1 | FTFSDYAIHWV |
| 5 | TY21428 HCDR1 | FTFSNYGIHWV |
| 6 | TY21429 HCDR1 | YTFSNYAIHWV |
| 7 | TY21430 HCDR1 | YSITSGHHWAWI |
| 8 | TY21431 HCDR1 | FTFTDYAIHWV |
| 9 | TY21432 HCDR1 | YTFSSYAIHWV |
| 10 | TY21433 HCDR1 | FTFSNYAIHWV |
| 11 | TY21371 HCDR2 | VSVISGYGSSTYYADSVKGRF |
| 12 | TY21372 HCDR2 | VSVISGYGSTTYYADSVKGRF |
| 13 | TY21373 HCDR2 | VSSISGYGSSTYYADSVKGRF |
| 14 | TY21375 HCDR2 | VSVISGYGGSTYYADSVKGRF |
| 15 | TY21428 HCDR2 | VSVISGYGGSTYYADSVKGRF |
| 16 | TY21429 HCDR2 | VSAISGTGSSTYYADSVKGRF |
| 17 | TY21430 HCDR2 | VSSISGSGSTTYYADSVKGRF |
| 18 | TY21431 HCDR2 | VSVISGYGSSTYYADSVKGRF |
| 19 | TY21432 HCDR2 | VSVISGAGSSTYYADSVKGRF |

-continued

| SEQ ID NO: | Description | Sequence |
|---|---|---|
| 20 | TY21433 HCDR2 | VSVISGYGSTTYYADSVKGRF |
| 21 | TY21371 HCDR3 | ARDPGVGGFDV |
| 22 | TY21372 HCDR3 | ARASSYGGFDY |
| 23 | TY21373 HCDR3 | ARGAYGYFDY |
| 24 | TY21375 HCDR3 | ARSGGGGYYFDY |
| 25 | TY21428 HCDR3 | ARRGLTSTYFDY |
| 26 | TY21429 HCDR3 | ARHSHSRYAFDY |
| 27 | TY21430 HCDR3 | ARGSYYGAGSFDY |
| 28 | TY21431 HCDR3 | ARGSYSSVYFDV |
| 29 | TY21432 HCDR3 | ARRTPAGNYFDY |
| 30 | TY21433 HCDR3 | ARSTVATPFAY |
| 31 | TY21371 LCDR1 | RASQSVRRRFLA |
| 32 | TY21372 LCDR1 | RASQDVSTAVA |
| 33 | TY21373 LCDR1 | PASSSVSYIH |
| 34 | TY21375 LCDR1 | RASQGIRSYLA |
| 35 | TY21428 LCDR1 | RASQSVGSWLA |
| 36 | TY21429 LCDR1 | RASHVRTAVA |
| 37 | TY21430 LCDR1 | RASQGITSALA |
| 38 | TY21431 LCDR1 | KASQDVRTAVA |
| 39 | TY21432 LCDR1 | RASQGISRWLA |
| 40 | TY21433 LCDR1 | KASQDVRTAVA |
| 41 | TY21371 LCDR2 | DASSLESGV |
| 42 | TY21372 LCDR2 | DASNRATGI |
| 43 | TY21373 LCDR2 | DASNLETGV |
| 44 | TY21375 LCDR2 | AASSLQSGV |
| 45 | TY21428 LCDR2 | DASNLETGV |
| 46 | TY21429 LCDR2 | DASNLETGV |
| 47 | TY21430 LCDR2 | DASSLESGV |
| 48 | TY21431 LCDR2 | AASSLQSGV |
| 49 | TY21432 LCDR2 | DASSLESGV |
| 50 | TY21433 LCDR2 | AASTLQSGV |
| 51 | TY21371 LCDR3 | YCQQYYPIPRT |
| 52 | TY21372 LCDR3 | YCQQYYPWPWT |
| 53 | TY21373 LCDR3 | YCQQYYPWPWT |
| 54 | TY21375 LCDR3 | YCQQSYHWPLT |
| 55 | TY21428 LCDR3 | YCQQSYPIPPT |
| 56 | TY21429 LCDR3 | YCQQYYPWPWT |
| 57 | TY21430 LCDR3 | YCQQYYPWPWT |

-continued

| DESERIPTION OF THE SEQUENCES | | |
| --- | --- | --- |
| SEQ ID NO: | Description | Sequence |
| 58 | TY21431 LCDR3 | YCQQSYPIPFT |
| 59 | TY21432 LCDR3 | YCEQYLEVPPT |
| 60 | TY21433 LCDR3 | YCQQSYPWPWT |
| 61 | TY21371 VH | EVQLVESGGGLVQPGGSLRLSCAASGFTFSGYAIHWVRQA PGKGLEWVSVISGYGSSTYYADSVKGRFTISRDNSKNTLYL QLNSLRAEDTAVYYCARDPGVGGFDVWGQGTLVTVSS |
| 62 | TY21372 VH | EVQLVESGGGLVQPGGSLRLSCAASGYTFSDYAIHWVRQA PGKGLEWVSVISGYGSTTYYADSVKGRFTISRDNSKNTLYL QLNSLRAEDTAVYYCARASSYGGFDYWGQGTLVTVSS |
| 63 | TY21373 VH | EVQLVESGGGLVQPGGSLRLSCAASGYSISSGYYWGWIRQ APGKGLEWVSSISGYGSSTYYADSVKGRFTISRDNSKNTLY LQLNSLRAEDTAVYYCARGAYGYFDYWGQGTLVTVSS |
| 64 | TY21375 VH | EVQLVESGGGLVQPGGSLRLSCAASGFTFSDYAIHWVRQA PGKGLEWVSVISGYGGSTYYADSVKGRFTISRDNSKNTLY LQLNSLRAEDTAVYYCARSGGGGYYFDYWGQGTLVTVSS |
| 65 | TY21428 VH | EVQLVESGGGLVQPGGSLRLSCAASGFTFSNYGIHWVRQA PGKGLEWVSVISGYGGSTYYADSVKGRFTISRDNSKNTLY LQLNSLRAEDTAVYYCARRGLTSTYFDYWGQGTLVTVSS |
| 66 | TY21429 VH | EVQLVESGGGLVQPGGSLRLSCAASGYTFSNYAIHWVRQA PGKGLEWVSAISGTGSSTYYADSVKGRFTISRDNSKNTLYL QLNSLRAEDTAVYYCARHSHSRYAFDYWGQGTLVTVSS |
| 67 | TY21430 VH | EVQLVESGGGLVQPGGSLRLSCAASGYSITSGHHWAWIRQ APGKGLEWVSSISGSGSTTYYADSVKGRFTISRDNSKNTLY LQLNSLRAEDTAVYYCARGSYYGAGSFDYWGQGTLVTVS S |
| 68 | TY21431 VH | EVQLVESGGGLVQPGGSLRLSCAASGFTFTDYAIHWVRQA PGKGLEWVSVISGYGSSTYYADSVKGRFTISRDNSKNTLYL QLNSLRAEDTAVYYCARGSYSSVYFDVWGQGTLVTVSS |
| 69 | TY21432 VH | EVQLVESGGGLVQPGGSLRLSCAASGYTFSSYAIHWVRQA PGKGLEWVSISGAGSSTYYADSVKGRFTISRDNSKNTLYL QLNSLRAEDTAVYYCARRTPAGNYFDYWGQGTLVTVSS |
| 70 | TY21433 VH | EVQLVESGGGLVQPGGSLRLSCAASGFTFSNYAIHWVRQA PGKGLEWVSVISGYGSTTYYADSVKGRFTISRDNSKNTLYL QLNSLRAEDTAVYYCARSTVATPFAYWGQGTLVTVSS |
| 71 | TY21371 VL | DIQLTQSPSSLSASVGDRVTITCRASQSVRRRFLAWYQQKP GKAPKLLIYDASSLESGVPSRFSGSGSGTDFTLTISSLQPEDF ATYYCQQYYPIPRTFGQGTKVEIK |
| 72 | TY21372 VL | DIQLTQSPSSLSASVGDRVTITCRASQDVSTAVAWYQQKPG KAPKLLIYDASNRATGIPSRFSGSGSGTDFTLTISSLQPEDFA TYYCQQYPWPWTFGQGTKVEIK |
| 73 | TY21373 VL | DIQLTQSPSSLSASVGDRVTITCPASSSVSYIHWYQQKPGKA PKLLIYDASNLETGVPSRFSGSGSGTDFTLTISSLQPEDFATY YCQQYPWPWTFGQGTKVEIK |
| 74 | TY21375 VL | DIQLTQSPSSLSASVGDRVTITCRASQGIRSYLAWYQQKPG KAPKLLIYAASSLQSGVPSRFSGSGSGTDFTLTISSLQPEDFA TYYCQQSYHWPLTFGQGTKVEIK |
| 75 | TY21428 VL | DIQLTQSPSSLSASVGDRVTITCRASQSVGSWLAWYQQKPG KAPKLLIYDASNLETGVPSRFSGSGSGTDFTLTISSLQPEDF ATYYCQQSYPIPPTFGQGTKVEIK |
| 76 | TY21429 VL | DIQLTQSPSSLSASVGDRVTITCRASHVRTAVAWYQQKPGK APKLLIYDASNLETGVPSRFSGSGSGTDFTLTISSLQPEDFAT YYCQQYPWPWTFGQGTKVEIK |
| 77 | TY21430 VL | DIQLTQSPSSLSASVGDRVTITCRASQGITSALAWYQQKPG KAPKLLIYDASSLESGVPSRFSGSGSGTDFTLTISSLQPEDFA TYYCQQYYPWPWTFGQGTKVEIK |

-continued

DESERIPTION OF THE SEQUENCES

| SEQ ID NO: | Description | Sequence |
|---|---|---|
| 78 | TY21431 VL | DIQLTQSPSSLSASVGDRVTITCKASQDVRTAVAWYQQKPG<br>KAPKLLIYAASSLQSGVPSRFSGSGSGTDFTLTISSLQPEDFA<br>TYYCQQSYPIPFTFGQGTKVEIK |
| 79 | TY21432 VL | DIQLTQSPSSLSASVGDRVTITCRASQGISRWLAWYQQKPG<br>KAPKLLIYDASSLESGVPSRFSGSGSGTDFTLTISSLQPEDFA<br>TYYCEQYLEVPPTFGQGTKVEIK |
| 80 | TY21433 VL | DIQLTQSPSSLSASVGDRVTITCKASQDVRTAVAWYQQKPG<br>KAPKLLIYAASTLQSGVPSRFSGSGSGTDFTLTISSLQPEDFA<br>TYYCQQSYPWPWTFGQGTKVEIK |
| 81 | TAC2188 VH | QVQLVQSGAEVKKPGASVKVSCKASGYTFTSYDISWVRQ<br>APGQGLEWMGVIWTDGGTNYAQKLQGRVTMTTDTSTSTA<br>YMELRSLRSDDTAVYYCARDQRLYFDVWGQGTTVTVSS |
| 82 | TAC2188 VL | DIQMTQSPSSLSASVGDRVTITCRASEDVNTYVSWYQQKP<br>GKAPKLLIYAASNRYTGVPSRFSGSGSGTDFTLTISSLQPED<br>FATYYCQQSFSYPTFGQGTKLEIK |
| 83 | TAC2205 VH | QVQLVQSGAEVKKPGSSVKVSCKASGYTFTDNYMIWVRQ<br>APGQGLEWMGDINPYNGGTTFNQKFKGRVTITADKSTSTA<br>YMELSSLRSEDTAVYYCARESPYFSNLYVMDYWGQGTLV<br>TVSS |
| 84 | TAC2205 VL | EIVLTQSPATLSLSPGERATLSCKASQSVDYDGDNYMNWY<br>QQKPGQAPRLLIYAASNLESGIPARFSGSGSGTDFTLTISSLE<br>PEDFAVYYCHLSNEDLSTFGGGTKVEIK |

EXAMPLES

Discovery of Primary Fabs that Specifically Bind to Human CSF-1R

Proprietary phagemid libraries (See PCT International Application titled "Dynamic Human Antibody Light Chain Libraries" filed concurrently herewith publication number WO 2019/036856, incorporated herein by reference in its entirety; See also PCT International Application titled "Dynamic Human Heavy Chain Antibody Libraries" filed concurrently herewith publication number WO 2019/036842, incorporated herein by reference in its entirety) were employed to pan against human CSF-1R antigen (RefSeq ID NP_005202). A total of three rounds of panning were conducted. After the final round of panning, single-colony supernatant ELISA was performed to identify the primary hits that specifically recognize human CSF-1R. The primary hits were defined as those whose ELISA signals were at least twice that of background. The coding regions for VH and VL of each primary hit were sequenced, the unique clones (as Fabs) were expressed in *E. coli* and purified for affinity measurement by ForteBio Octet RED96 Systems. Briefly, the AHC sensors (Anti-Human IgG Fc Capture Dip and Read Biosensors) were used to capture human CSFIR-Fc (Acrobiosystem, CSR-H5258), and dipped into wells containing purified Fabs that were serially diluted with kinetic buffer. The acquired ForteBio data were processed with Data Acquisition software 7.1, and kinetic data were fitted to a 1:1 Langmuir binding model. There are a total of 53 hits that meet the following criteria: response signal higher than 0.1, $R^2 > 0.894$ and affinity $K_D < 40$ nM. 12 of them were then converted into human IgG4 (Uniprot P01861) or IgG1 (Uniprot P01857) for detailed biophysical and functional characterization.

IgG Conversion and Expression

The heavy and light chains of the selected primary hits were cloned into a mammalian expression vector separately in human IgG4 isotype with S241P mutation. The heavy and light chains of two reference antibodies (TAC2188 as described in U.S. Pat. No. 8,206,715 and TAC2205 as described in WO 2013/132044) were also cloned in the same manner. The converted IgGs were listed in Table 1. The heavy and light chain variable regions of the two reference antibodies are listed above.

Pairs of heavy and light chain-containing plasmids were transiently transfected into HEK293F cells following manufacturer's instructions. The supernatants were harvested, cleared by centrifugation and filtration, and IgGs were purified with standard protein A affinity chromatography (MabSelect SuRe, GE Healthcare). The proteins were eluted and neutralized, and buffer exchanged into 20 mM Histidine buffer, (pH 5.5). Protein concentrations were determined by UV-spectrophotometry, and IgG purity was analyzed under denaturing, reducing and non-reducing conditions by SDS-PAGE or SEC-HPLC.

Epitope Characterization

The epitopes of test antibodies were characterized by ForteBio. The reference antibody TAC2188 was biotinylated with EZ-Link Sulfo-NHS-Biotinylation Kit (Thermo Fisher Scientific #21525) according to manufacturer's instructions. Afterwards, the biotinylated reference antibody TAC2188 was diluted with KB buffer (PBS buffer supplemented with 0.02% Tween 20 and 0.1% BSA) and loaded onto SA sensors (Pall, 185019). The biosensors were then dipped first into wells containing human CSF1R-His in KB buffer (100 nM), then into wells containing test antibodies (including the other reference antibody, TAC2205) in KB buffer (100 nM). Increase of response indicates that the test antibody binds to a different epitope on human CSF-1R than the immobilized antibody. As shown in Table 1, the two reference antibodies TAC2188 and TAC2205 bind to different epitopes on CSF-1R, consistent with published data. Interestingly, the test antibodies all compete with TAC2188 for binding to human CSF-1R.

TABLE 1

| Binding affinity and epitope characterization of converted IgG. | | |
|---|---|---|
| | Human CSF-1R $K_D$ (nM) BIAcore | Epitope overlapping with TAC2188 |
| TAC2188 | 1.66 | — |
| TAC2205 | 0.67 | No |
| TY21371 | 0.60 | Yes |
| TY21372 | 1.61 | Yes |
| TY21373 | 23.60 | Yes |
| TY21375 | 35.50 | Yes |
| TY21428 | 9.86 | Yes |
| TY21429 | 3.18 | Yes |
| TY21430 | 8.35 | Yes |
| TY21431 | 20.9 | Yes |
| TY21432 | 13.8 | Yes |
| TY21433 | 3.51 | Yes |

Binding Affinity Characterization

The specific binding affinity and kinetics of antibodies against human CSF-1R protein were examined by surface plasmon resonance (SPR) analysis using a Biacore™ T200 instrument (GE, USA) according to the manufacturer's guidelines. Anti-Human IgG (Fc) antibody (Sigma, I2136) was immobilized on CM5 chips according to the instructions of Amine Coupling kit (GE Biacore #BR-1000-50). The immobilized Anti-Human IgG (Fc) antibody was used to capture the antibodies. 8 different concentrations (0.78, 1.56, 3.13, 6.25, 12.5, 25, 50, 100) (nM) (diluted in running buffer) of human CSF-1R (human CSF1R-His, Acrobiosystem, CSR-H5228) were injected at a flow rate of 30 µl/min for 300 seconds, and the dissociation time was 300 seconds. The running buffer used was 0.01 M HEPES, 0.15 M NaCl, 3 mM EDTA, 0.05% (v/v) surfactant P20, pH 7.4. Corresponding controls were conducted in each case using a blank flow cell with no protein captured for "background" subtraction. The association and dissociation curves were fitted to a 1:1 Langmuir binding model using Biacore T200 Evaluation Software (GE, USA) according to the manufacturer's guidelines. As listed in Table 1, the antibodies bind human CSF-1R with affinities ranging from 0.67 nM (TY21371) to 35.5 nM (TY21375).

The specificities of the antibodies were also assessed against human, monkey and mouse CSF-1R that are transiently expressed on the surface of HEK293F cells (FIG. 1). Briefly, HEK293F cells were transfected with a plasmid expressing full-length human, monkey (RefSeq ID XP_015307616) or mouse (RefSeq ID NP_001032948) CSF-1R from a bicistronic IRES vector. EGFP was used to identify the transfected cells. After 40 hrs, the transfected cells were harvested and then washed once with 1% PBSA buffer (1% (w/v) BSA in 1×PBS). Cells were then incubated with various IgGs (each at 100 nM) for 1 hr at room temperature, washed once with pre-chilled 1% PBSA buffer, and incubated with Alexa Fluor® 647 conjugated mouse anti-human Fc antibodies for 30 min on ice. The cells were washed once prior to analysis by flow cytometry (Beckman® CytoFlex). As shown in FIG. 1, all antibodies demonstrated binding to human and monkey CSF-1R, but none of them binds to mouse CSF-1R.

Developability Profile of Antibodies

For developability assessment, purified TAC2188, TY21371, TY21372 and TY21432 were exchanged into storage buffer (20 mM histidine, pH 5.5). All experiments, including solubility, stability under accelerated stress conditions, and differential scanning fluorescence (DSF) tests, were performed in storage buffer. For all the SEC-HPLC analyses, the TSKgel columns (Tosoh Bioscience G3000SWxl) were used.

Solubility

TY21371, TY21372 and TY21432 were concentrated to higher than 80 mg/ml in storage buffer without obvious precipitation (Table 2). They were further analyzed through SEC-HPLC for the presence of high molecular weight (HMW) aggregate. As shown in Table 2, no significant increase of HMW aggregate was observed at high concentration.

TABLE 2

| High solubility of antibodies. | | | | |
|---|---|---|---|---|
| ID | Concentration (mg/mL) | HMW (%) (1 mg/ml) | HMW (%) High concentration | Δ HMW (%) |
| TAC2188 | 78.3 | 15.11 | 15.12 | 0.01 |
| TY21371 | 85.3 | 1.74 | 2.14 | 0.4 |
| TY21372 | 134.8 | 6.41 | 7.17 | 0.76 |
| TY21432 | 129.9 | 1.54 | 1.81 | 0.27 |

Antibody Stability Under Accelerated Stress Conditions

Figure 2:
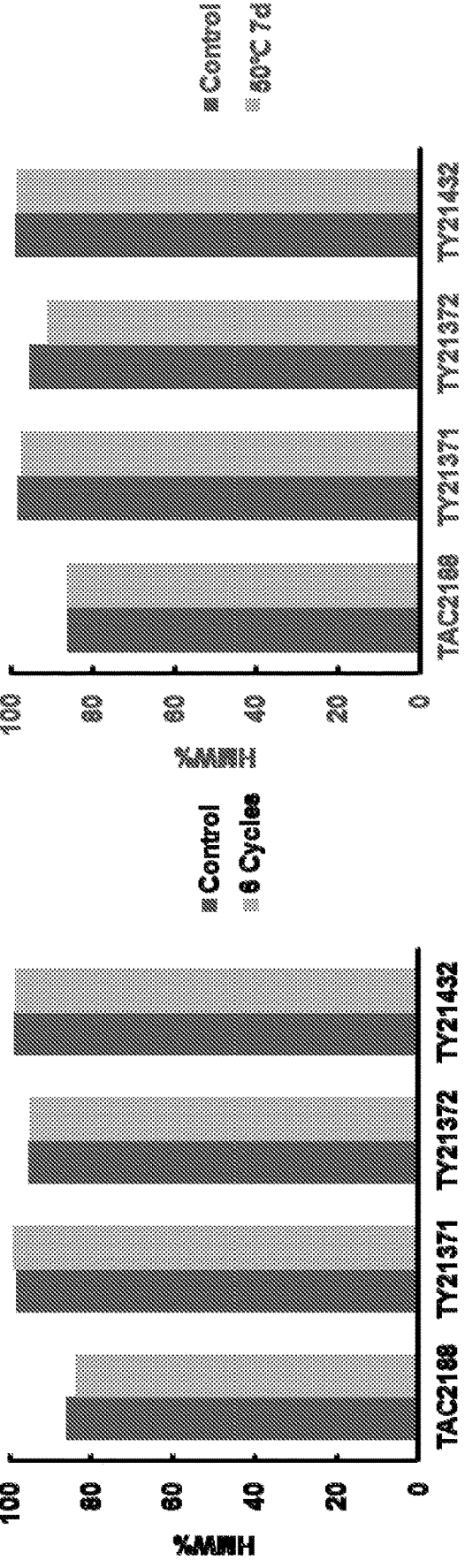
FIG. 2 shows the stability of the antibodies after 6 cycles of freezing and thawing (left panel) or storage at 50° C. for 7 days (right panel).

Antibody stabilities were also examined under accelerated stress conditions. As shown in FIG. 2, the antibodies TY21371, TY21372 and TY21432 remain stable after 6 cycles of freezing (−80° C.) and thawing (at room temperature). Also the antibodies TY21371, TY21372 and TY21432 remain stable after seven days at 50° C. There were almost no increase of HMW aggregate or LMW fragments except TY21372.

Inhibition of CSF-1 Induced CSF-1R Phosphorylation

CSF-1 (RefSeq ID NP_000748) can activate a cellular signaling through inducing the phosphorylation of its receptor, CSF-1R. To evaluate the activity of various anti-CSF1R antibodies including TY21371, TY21372, TY21432, and reference antibody TAC2188 to inhibit CSF-1R phosphorylation induced by CSF-1, a Phospho-ELISA assay was performed. Briefly, 293T cells were transfected with human CSF-1R expressing plasmid. 4 hrs post transfection, cells were split into 96-well plate at $2 \times 10^4$ cells/well and cultured for 18 hrs to allow cell adherence and CSF-1R expression, in a 5% $CO_2$ incubator at 37° C. Then the cell supernatant was discarded, and serial diluted test antibodies were added into the plate and incubated for 30 min at 37° C. The unbound antibody solution was discarded and the cells were incubated with 50 ng/ml M-CSF for another 5 min. The cells were then immediately washed with DPBS and lysed. The CFS1R phosphorylation level in the cell lysate was analyzed with the human phospho M-CSFR ELISA kit (R&D) following the manufacture's instruction, and signals were measured with the SpectraMax i3x microplate reader at 450 nm.

Figure 3:
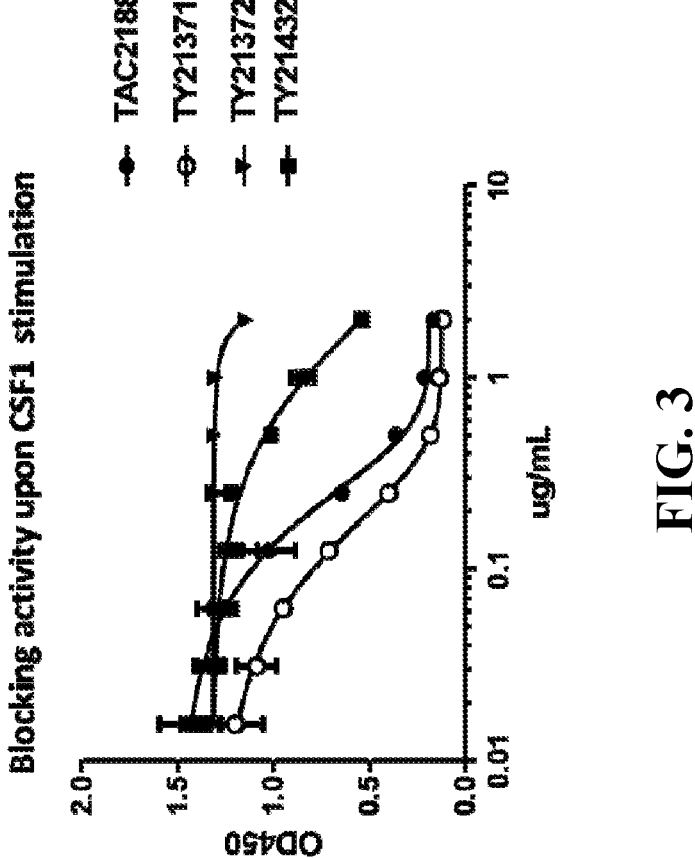
FIG. 3 shows the inhibition of CSF-1-induced CSF-1R phosphorylation by the antibodies.

As shown in FIG. 3, the reference antibody TAC2188, as well as TY21371 and TY21432 can inhibit CSF-1R phosphorylation upon CSF-1 stimulation in a dose dependent manner. TY21371 exhibits much stronger inhibition of CSF-1R phosphorylation than the reference antibody TAC2188 and other tested antibodies.

Inhibition of IL-34 Induced CSF-1R Phosphorylation

As another ligand for CSF-1R, IL-34 (RefSeq ID NP_001166243) can also activate CSF-1R mediated cellular signaling through inducing the phosphorylation of CSF-1R. To evaluate the activity of various anti-CSF1R antibodies to inhibit CSF-1R phosphorylation induced by IL-34, a Phospho-ELISA was performed. Briefly, 293T cells were transfected with human CSF-1R expressing plasmid. 4 hrs post transfection, cells were split into 96-well plate at $2\times10^4$ cells/well and cultured for 18 hrs to allow cell adherence and CSF-1R expression, in a 5% $CO_2$ incubator at 37° C. Then the cell supernatant was discarded, and serial diluted test antibodies were added into the plate and incubated for 30 min at 37° C. The unbound antibody solution was discarded and the cells were incubated with 100 ng/mL IL-34 for another 5 min. The cells were then immediately washed with DPBS and lysed. The CFS1R phosphorylation level in the cell lysate was analyzed with the human phospho M-CSFR ELISA kit (R&D) following the manufacture's instruction, and signals were measured with the SpectraMax i3x microplate reader at 450 nm.

Figure 4:
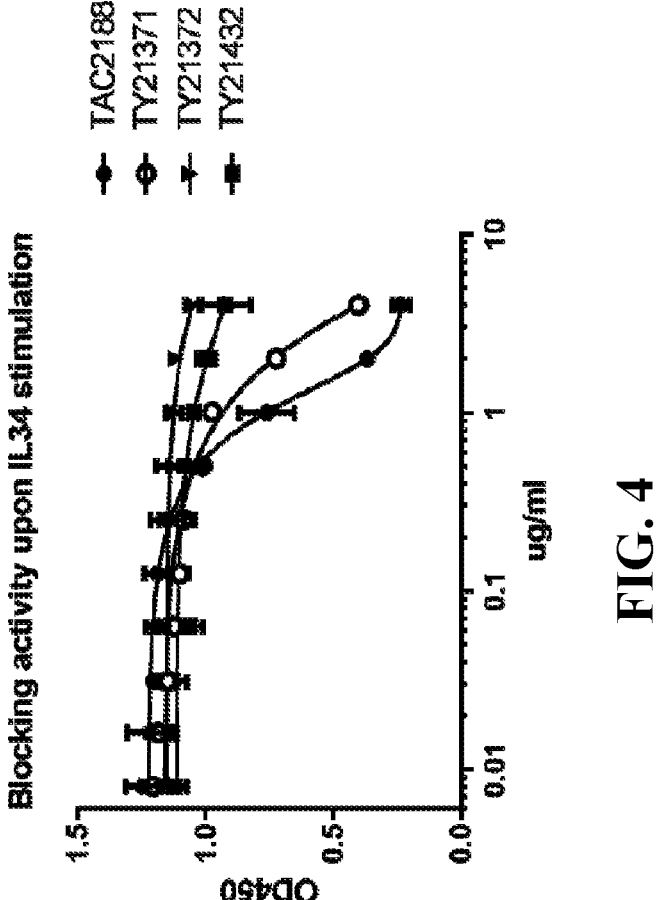
FIG. 4 shows the inhibition of IL-34-induced CSF-1R phosphorylation by the antibodies.

As shown in FIG. 4, TAC2188 strongly blocks CSF-1R phosphorylation upon IL-34 stimulation, while TY21371 is slightly less potent, and TY21432 or TY21372 demonstrates weak inhibition of CSF-1R phosphorylation upon IL-34 stimulation.

Inhibition of Monocyte Proliferation Induced by CSF-1

Figure 5:
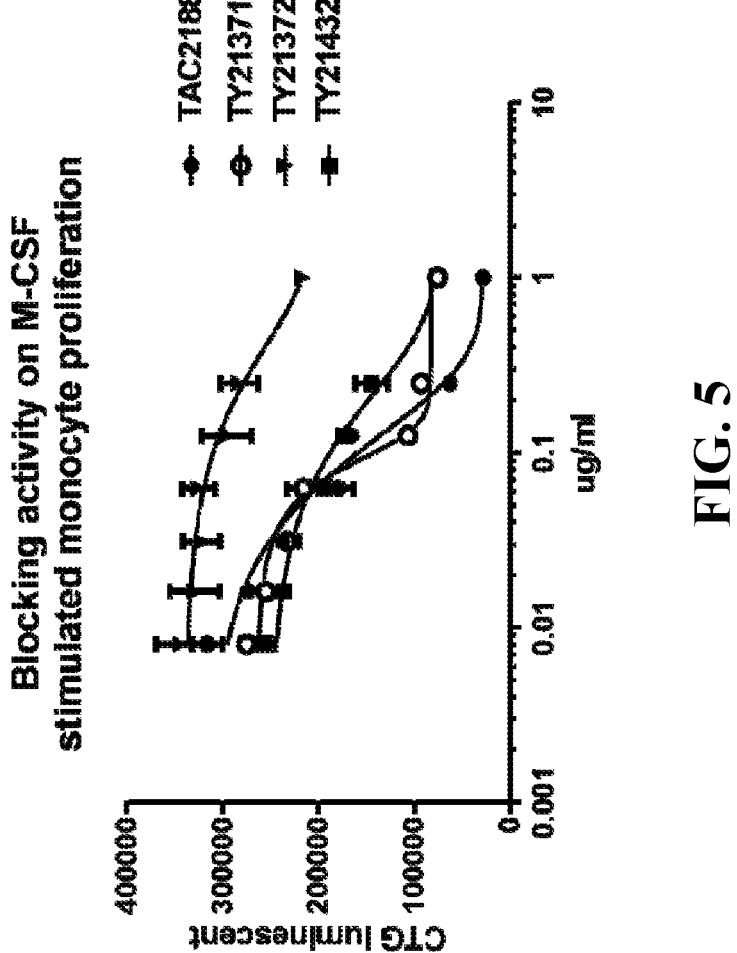
FIG. 5 shows the inhibition of CSF-1-induced monocyte proliferation by the antibodies.

CD14 positive monocytes were isolated with EasySep Human CD14 Positive Selection Kit (StemCell Technologies) according to the manufacture's instruction. Cells were prepared at a density of $3\times10^5$ cells/mL in RPMI1640 complete medium. 100 µL of cell suspension was plated to each assay wells and incubated with serial diluted antibodies for 30 min at 37° C. Then 50 ng/ml M-CSF solution was added into assay wells and incubated with the cells for another 5 days in a 37° C., 5% $CO_2$ incubator. Monocyte proliferation was analyzed using Cell Titer Glo kit (Promega). As shown in FIG. 5, the reference antibody TAC2188 strongly inhibits M-CSF stimulated monocyte proliferation, while TY21371 exhibits better blocking activity than TY21372 and TY21432.

Inhibition of Monocyte Proliferation Induced by IL-34

Figure 6:
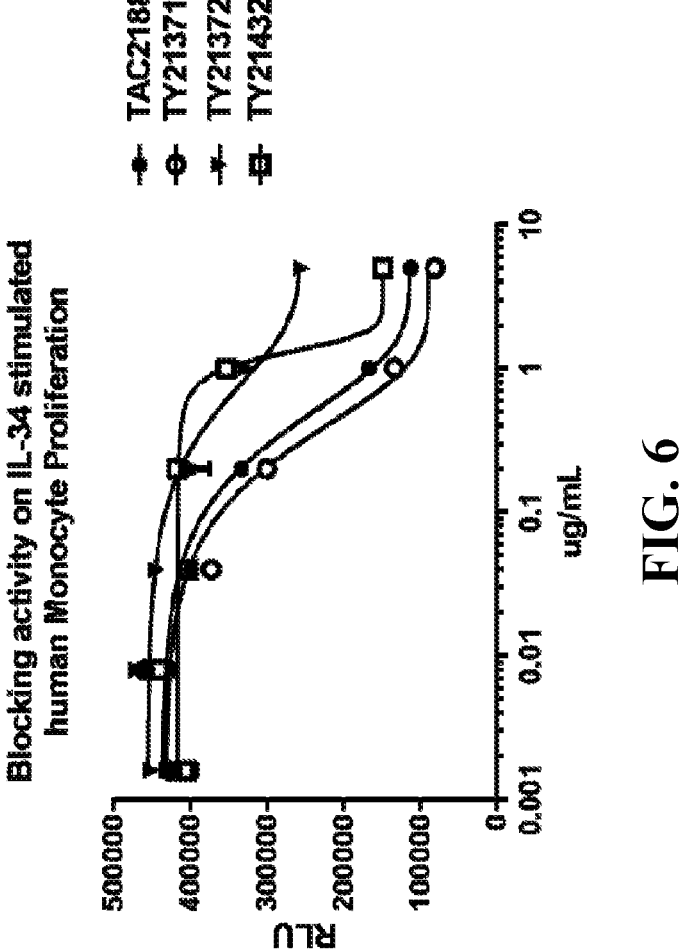
FIG. 6 shows the inhibition of IL-34-induced monocyte proliferation by the antibodies.

CD14 positive monocytes were isolated with EasySep Human CD14 Positive Selection Kit (StemCell Technologies) according to the manufacture's instruction. Cells were prepared at a density of $1\times10^6$ cells/mL in RPMI1640 complete medium. 50 µL of cell suspension was plated to each assay wells supplemented with 100 ng/mL IL-34. Monocytes were incubated with serial diluted antibodies for 5 days in a 37° C., 5% $CO_2$ incubator. Monocyte proliferation was analyzed using Cell Titer Glo kit (Promega). As shown in FIG. 6, both the reference antibody TAC2188 and the test antibody TY21371 can potently inhibit IL-34 stimulated monocyte proliferation. TY21371 exhibits even stronger inhibition than the reference antibody TAC2188.

Pharmacokinetics Study in Cynomolgus Monkey

Figure 7:
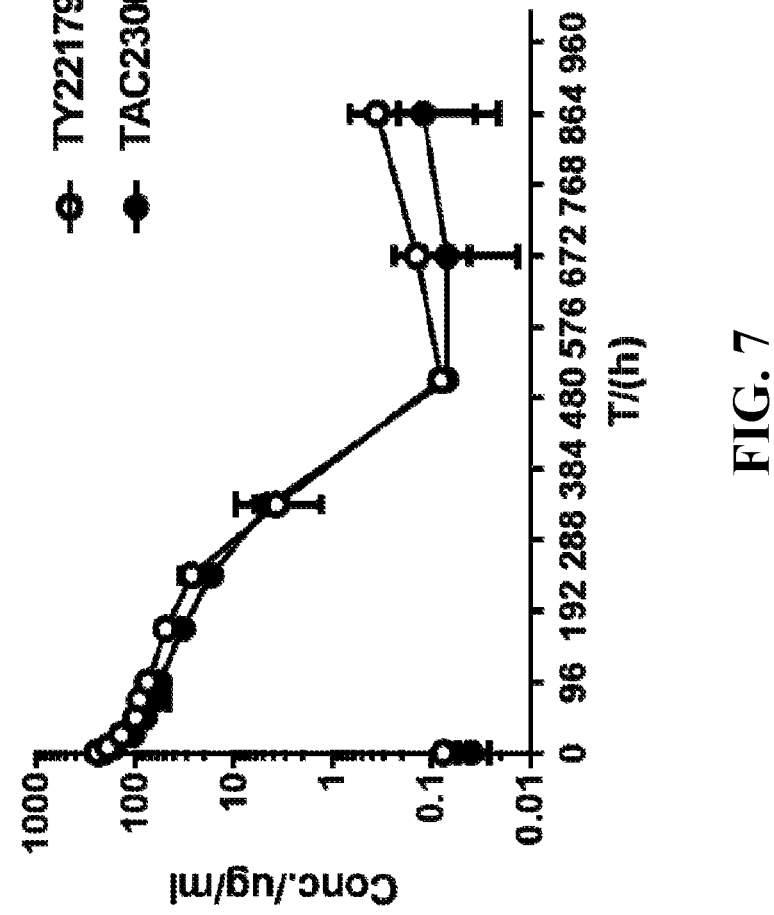
FIG. 7 shows the PK profile of the antibodies in cynomolgus monkeys after an i.v. dose of 10 mg/kg.

A pharmacokinetic study of TY22179 (i.e., the IgG1 format of TY21371) and TAC2300 (i.e., the IgG1 format of TAC2188) was conducted in naive cynomolgus monkeys by intravenous infusion at a dose of 10 mg/kg. Each drug was studied in one group of cynomolgus monkeys containing 1 male and 1 female. Serum samples were collected at predose, 0.25 hr, 1 hr, 8 hr, 24 hrs, 48 hrs, 96 hrs, 120 hrs, 168 hrs, 240 hrs, 336 hrs, 504 hrs, 672 hrs and 864 hrs post dosing. Serum drug concentrations of TY22179 and TAC2300 were analyzed by ELISA, in which antigen-Fc fusion was used for capture and the HRP-labeled anti-human IgG (Fab specific) antibody for detection. As shown in FIG. 7, TY22179 exhibited similar PK profile as the reference antibody TAC2300. Systemic exposures were achieved in all monkeys following i.v. infusion. Mean $C_{max}$ was 249 µg/mL or 242 µg/mL, mean $AUC_{0-864\ h}$ was 20058 µg·h/mL or 15103 µg·h/mL, the half-life ($t_{1/2}$) was 54-103 h or 79-89 h, for TY22179 and TAC2300, respectively.

Pharmacodynamic Effects in Cynomolgus Monkey

Figure 8:
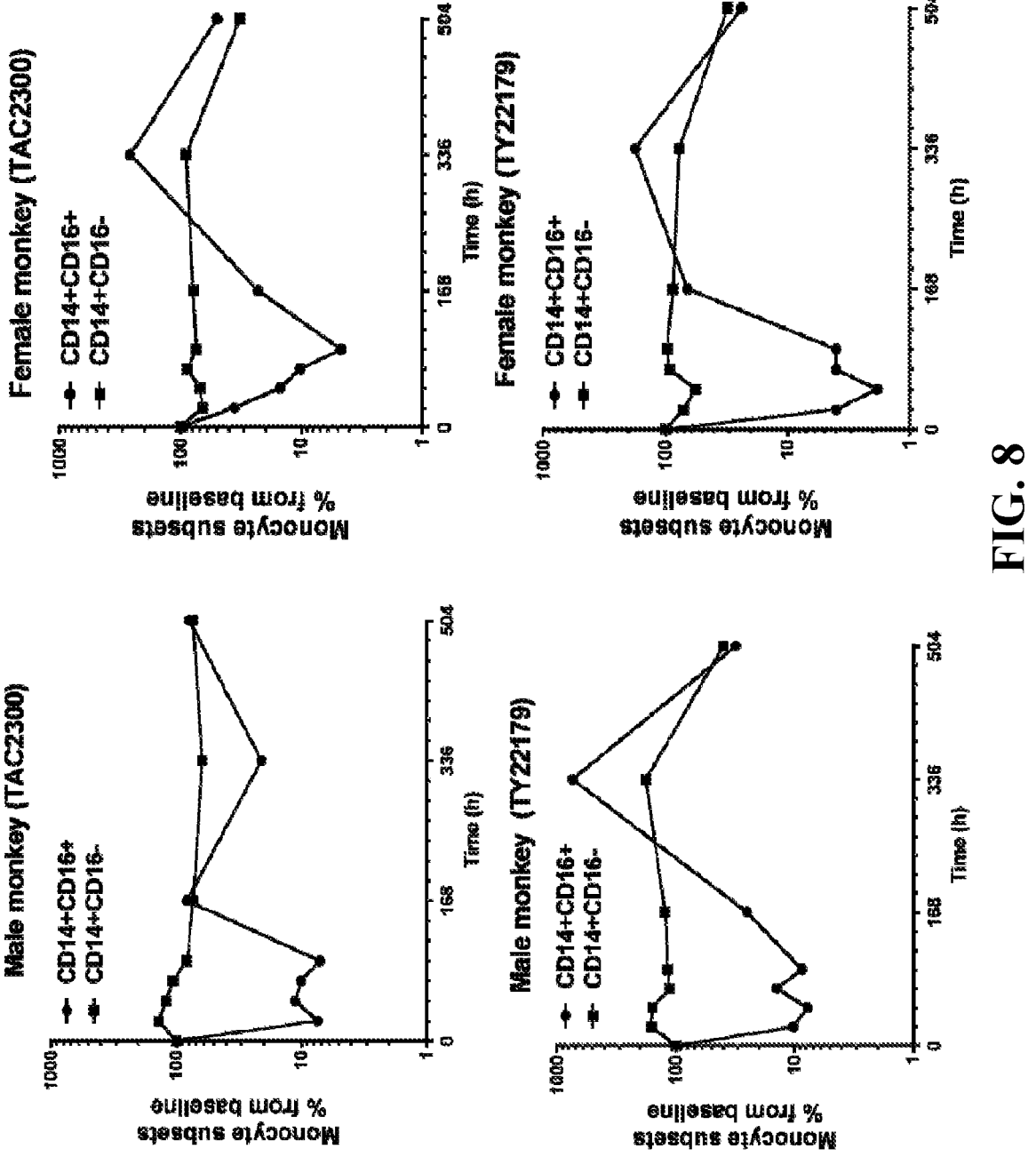
FIG. 8 shows the change in the number of CD14+CD16+ and CD14 CD16-monocytes in cynomolgus monkeys after an i.v. dose of 10 mg/kg.
Figure 9:
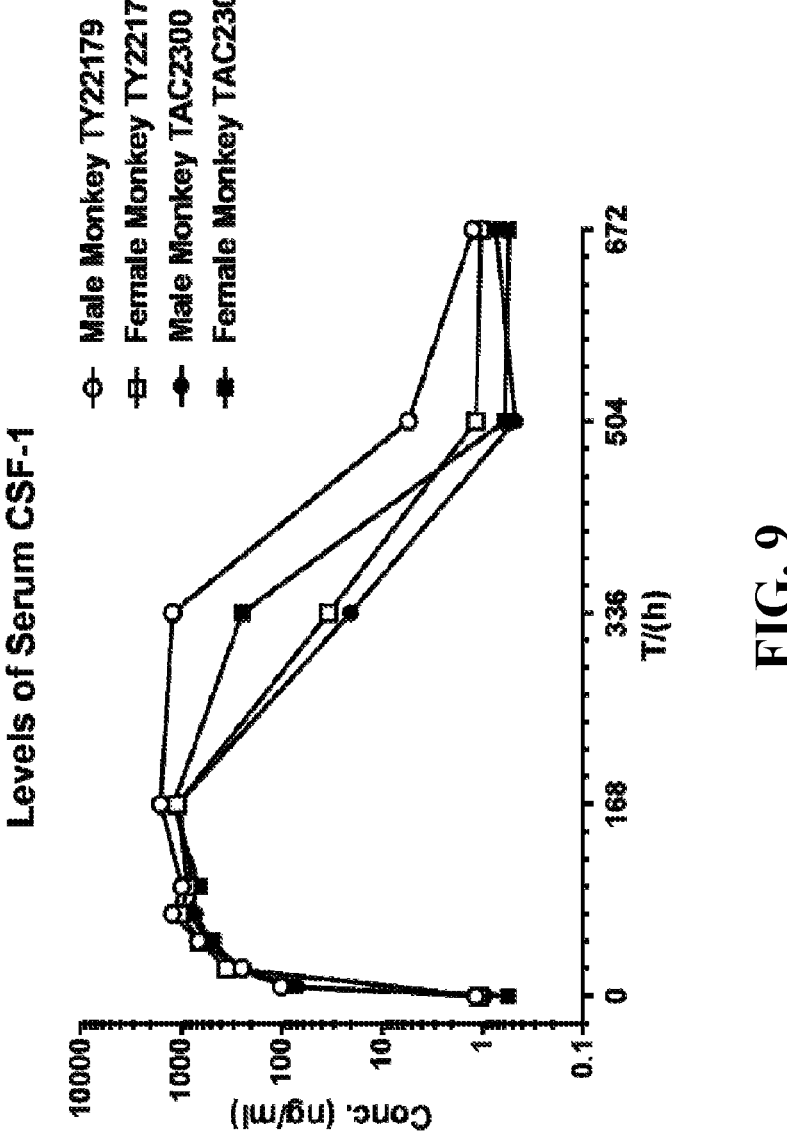
FIG. 9 shows the change in the serum CSF-1 level in cynomolgus monkeys after an i.v. dose of 10 mg/kg.

A pharmacodynamic study of TY22179 was conducted in naive cynomolgus monkeys. A single dose (10 mg/kg) of TY22179 or the reference antibody TAC2300 was intravenously administrated to one group of monkeys. Each group contains 1 male and 1 female. Whole blood samples collected at the indicated time points were subjected to flow cytometry for analysis of nonclassical $CD14^+CD16^+$ and classical $CD14^+CD16^-$ monocytes. Serum levels of CSF-1 were also determined with an ELISA kit at different time points. As shown in FIG. 8, both TY22179 and the reference antibody TAC2300 mediated a rapid elimination of nonclassical $CD14^+CD16^+$, but not of classical $CD14^+CD16^-$ monocytes in periphery blood of cynomolgus monkeys in a similar pattern. This effect is consistent with the mechanism of action of these antibodies. A strong rebound effect on these monocytes occurred starting from one week post-dosing, likely due to a feedback mechanism with decay of TY22179 and reference antibody levels. This rebound was transient and nonclassical $CD14^+CD16^+$ monocytes returned to normal physiological level thereafter. As shown in FIG. 9, there was rapid increase of serum CSF-1 levels as early as 8 hrs post antibody dosing. The increase continued until reaching plateau at around one week post dosing, by which over 1000-fold CSF-1 levels were achieved compared to the pre-dose baseline. Then the levels of CSF-1 started a downtrend and returned to normal physiological levels by 3~4 weeks post dosing. This CSF-1 increase likely propelled the recovery of nonclassical monocytes after initial depletion.

---

The invention claimed is:

1. An isolated monoclonal antibody or an antigen-binding fragment thereof, which specifically binds to human colony stimulating factor 1 receptor (CSF-1R) and comprises (1) a heavy chain variable domain (VH) comprising a complementary determining region (CDR) 1 as set forth in SEQ ID NO: 1, a CDR2 as set forth in SEQ ID NO: 11 and a CDR3 as set forth in SEQ ID NO: 21, and a light chain variable domain (VL) comprising a CDR1 as set forth in SEQ ID NO: 31, a CDR2 as set forth in SEQ ID NO: 41 and a CDR3 as set forth in SEQ ID NO: 51;

(2) a VH comprising a CDR1 as set forth in SEQ ID NO: 2, a CDR2 as set forth in SEQ ID NO: 12 and a CDR3 as set forth in SEQ ID NO: 22, and a VL comprising a CDR1 as set forth in SEQ ID NO: 32, a CDR2 as set forth in SEQ ID NO: 42 and a CDR3 as set forth in SEQ ID NO: 52;

(3) a VH comprising a CDR1 as set forth in SEQ ID NO: 3, a CDR2 as set forth in SEQ ID NO: 13 and a CDR3 as set forth in SEQ ID NO: 23, and a VL comprising a CDR1 as set forth in SEQ ID NO: 33, a CDR2 as set forth in SEQ ID NO: 43 and a CDR3 as set forth in SEQ ID NO: 53;

(4) a VH comprising a CDR1 as set forth in SEQ ID NO: 4, a CDR2 as set forth in SEQ ID NO: 14 and a CDR3 as set forth in SEQ ID NO: 24, and a VL comprising a CDR1 as set forth in SEQ ID NO: 34, a CDR2 as set forth in SEQ ID NO: 44 and a CDR3 as set forth in SEQ ID NO: 54;

(5) a VH comprising a CDR1 as set forth in SEQ ID NO: 5, a CDR2 as set forth in SEQ ID NO: 15 and a CDR3 as set forth in SEQ ID NO: 25, and a VL comprising a CDR1 as set forth in SEQ ID NO: 35, a CDR2 as set forth in SEQ ID NO: 45 and a CDR3 as set forth in SEQ ID NO: 55;

(6) a VH comprising a CDR1 as set forth in SEQ ID NO: 6, a CDR2 as set forth in SEQ ID NO: 16 and a CDR3 as set forth in SEQ ID NO: 26, and a VL comprising a CDR1 as set forth in SEQ ID NO: 36, a CDR2 as set forth in SEQ ID NO: 46 and a CDR3 as set forth in SEQ ID NO: 56;

(7) a VH comprising a CDR1 as set forth in SEQ ID NO: 7, a CDR2 as set forth in SEQ ID NO: 17 and a CDR3 as set forth in SEQ ID NO: 27, and a VL comprising a CDR1 as set forth in SEQ ID NO: 37, a CDR2 as set forth in SEQ ID NO: 47 and a CDR3 as set forth in SEQ ID NO: 57;

(8) a VH comprising a CDR1 as set forth in SEQ ID NO: 8, a CDR2 as set forth in SEQ ID NO: 18 and a CDR3 as set forth in SEQ ID NO: 28, and a VL comprising a CDR1 as set forth in SEQ ID NO: 38, a CDR2 as set forth in SEQ ID NO: 48 and a CDR3 as set forth in SEQ ID NO: 58;

(9) a VH comprising a CDR1 as set forth in SEQ ID NO: 9, a CDR2 as set forth in SEQ ID NO: 19 and a CDR3 as set forth in SEQ ID NO: 29, and a VL comprising a CDR1 as set forth in SEQ ID NO: 39, a CDR2 as set forth in SEQ ID NO: 49 and a CDR3 as set forth in SEQ ID NO: 59; or

(10) a VH comprising a CDR1 as set forth in SEQ ID NO: 10, a CDR2 as set forth in SEQ ID NO: 20 and a CDR3 as set forth in SEQ ID NO: 30, and a VL comprising a CDR1 as set forth in SEQ ID NO: 40, a CDR2 as set forth in SEQ ID NO: 50 and a CDR3 as set forth in SEQ ID NO: 60.

2. The antibody or antigen-binding fragment according to claim 1, which comprises (1) a VH as set forth in SEQ ID NO: 61 and a VL as set forth in SEQ ID NO: 71;

(2) a VH as set forth in SEQ ID NO: 62 and a VL as set forth in SEQ ID NO: 72;

(3) a VH as set forth in SEQ ID NO: 63 and a VL as set forth in SEQ ID NO: 73;

(4) a VH as set forth in SEQ ID NO: 64 and a VL as set forth in SEQ ID NO: 74;

(5) a VH as set forth in SEQ ID NO: 65 and a VL as set forth in SEQ ID NO: 75;

(6) a VH as set forth in SEQ ID NO: 66 and a VL as set forth in SEQ ID NO: 76;

(7) a VH as set forth in SEQ ID NO: 67 and a VL as set forth in SEQ ID NO: 77;

(8) a VH as set forth in SEQ ID NO: 68 and a VL as set forth in SEQ ID NO: 78;

(9) a VH as set forth in SEQ ID NO: 69 and a VL as set forth in SEQ ID NO: 79; or

(10) a VH as set forth in SEQ ID NO: 70 and a VL as set forth in SEQ ID NO: 80.

3. The antibody or antigen-binding fragment according to claim 1, which specifically binds to human CSF-1R.

4. The antibody or antigen-binding fragment according to claim 1, which is a full length antibody of the IgG1 or IgG4 subclass.

5. The antibody or antigen-binding fragment according to claim 4, which is a full length antibody of the IgG4 subclass with the S241P mutation according to the EU numbering system.

6. The antibody or antigen-binding fragment according to claim 1, which is an antibody fragment selected from the group consisting of Fab, Fab', Fab-SH, F(ab')₂, scFv and diabody.

7. The antibody or antigen-binding fragment according to claim 1, which possesses one or more of the following properties;

(1) having an affinity for human CSF-1R with $K_D$<40 nM;

(2) binding to the overlapping epitope on human CSF-1R as an antibody comprising a VH as set forth in SEQ ID NO: 81 and a VL as set forth in SEQ ID NO: 82;

(3) binding to monkey CSF-1R;

(4) not binding to mouse CSF-1R;

(5) having a solubility higher than 80 mg/mL;

(6) having less than 10% HMW at high concentration, and ΔHMW less than 1% as compared with the 1 mg/ml solution;

(7) remaining stable after 6 cycles of freezing at −80° C. and thawing at room temperature;

(8) remaining stable after 7 days at 50° C.;

(9) inhibiting CSF-1R phosphorylation induced by CSF-1;

(10) inhibiting CSF-1R phosphorylation induced by IL-34;

(11) inhibiting monocyte proliferation induced by CSF-1;

(12) inhibiting monocyte proliferation induced by IL-34;

(13) having a mean $C_{max}$ greater than 200 μg/mL, a mean $AUC_{0\text{-}864\,h}$ greater than 15000 μg·h/mL, and/or a mean $t_{1/2}$ greater than 50 hrs at an i.v. dose of 10 mg/kg in cynomolgus monkey;

(14) mediating rapid elimination of $CD14^+CD16^+$ monocytes in periphery blood at an i.v. dose of 10 mg/kg in cynomolgus monkey; and/or

(15) mediating rapid increase of serum CSF-1 level at an i.v. dose of 10 mg/kg in cynomolgus monkey.

8. A pharmaceutical composition comprising the antibody or antigen-binding fragment thereof according to claim 1 and a pharmaceutically acceptable carrier.

9. A method of increasing CSF-1 levels in a subject comprising administrating a therapeutically effective amount of the antibody or antigen-binding fragment according to claim 1 to the subject.

10. The method of claim 9, wherein the subject has a CSF-1R mediated disease, disorder, or condition.

\* \* \* \* \*